US010850078B2

(12) United States Patent
Grace et al.

(10) Patent No.: US 10,850,078 B2
(45) Date of Patent: Dec. 1, 2020

(54) ELECTRICALLY-INDUCED FLUID FILLED BALLOON CATHETER

(71) Applicant: The Spectranetics Corporation, Colorado Springs, CO (US)

(72) Inventors: Kenneth P. Grace, Woodland Park, CO (US); Thomas Triffo, Colorado Springs, CO (US); James Cezo, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 829 days.

(21) Appl. No.: 14/984,294

(22) Filed: Dec. 30, 2015

(65) Prior Publication Data

US 2016/0184570 A1     Jun. 30, 2016

Related U.S. Application Data

(60) Provisional application No. 62/261,085, filed on Nov. 30, 2015, provisional application No. 62/257,404,
(Continued)

(51) Int. Cl.
| | | |
|---|---|---|
| A61M 25/10 | (2013.01) | |
| A61B 17/22 | (2006.01) | |
| A61M 37/00 | (2006.01) | |

(52) U.S. Cl.
CPC ..... *A61M 25/104* (2013.01); *A61B 17/22022* (2013.01); *A61B 2017/22007* (2013.01);
(Continued)

(58) Field of Classification Search
CPC .............. A61F 2/958; A61F 2002/9583; A61F 2002/9586; A61M 2025/1075; A61M 2025/1084
See application file for complete search history.

(56) References Cited

U.S. PATENT DOCUMENTS

| | | |
|---|---|---|
| 4,770,653 A | 9/1988 | Shturman |
| 4,785,806 A | 11/1988 | Deckelbaum |

(Continued)

FOREIGN PATENT DOCUMENTS

| | | |
|---|---|---|
| CN | 103462688 A | 12/2013 |
| DE | 2517019 A | 10/1976 |

(Continued)

OTHER PUBLICATIONS

International Search Report and Written Opinion issued in PCT/US2015/068161, dated May 4, 2016, 19 pages.
(Continued)

*Primary Examiner* — Wade Miles

(57) ABSTRACT

The present disclosure relates generally to the use of medical devices for the treatment of vascular conditions. In particular, the present disclosure provides devices and methods for using electrically-induced pressure waves to disrupt vascular blockages. The present disclosure not only provides devices and methods for using electrically-induced pressure waves to disrupt vascular blockages, but the present disclosure also provides devices and method for assisting the guidewire in penetrating an occlusion, devices and method for using a sealable valve in the tip of the balloon catheter to reduce the overall size and diameter of the balloon catheter, thereby allowing the balloon catheter to penetrate smaller size blood vessels and devices. Given the persistence of coronary artery disease (CAD) and peripheral artery disease (PAD), there remains a need for improved therapeutic methods designed not only to reduce vascular blockages in the short term, but also to prevent future complications such as restenosis.

8 Claims, 25 Drawing Sheets

Related U.S. Application Data filed on Nov. 19, 2015, provisional application No. 62/248,875, filed on Oct. 30, 2015, provisional application No. 62/248,913, filed on Oct. 30, 2015, provisional application No. 62/232,318, filed on Sep. 24, 2015, provisional application No. 62/209,691, filed on Aug. 25, 2015, provisional application No. 62/098,242, filed on Dec. 30, 2014.

(52) U.S. Cl.
CPC .............. *A61B 2017/22021* (2013.01); *A61B 2017/22024* (2013.01); *A61B 2017/22025* (2013.01); *A61B 2017/22051* (2013.01); *A61M 37/0092* (2013.01); *A61M 2025/105* (2013.01); *A61M 2025/1075* (2013.01); *A61M 2025/1081* (2013.01); *A61M 2025/1093* (2013.01); *A61M 2205/054* (2013.01)

(56) References Cited

U.S. PATENT DOCUMENTS

| | | | |
|---|---|---|---|
| 4,793,359 A | 12/1988 | Sharrow | |
| 4,832,023 A | 5/1989 | Murphy-Chutorian et al. | |
| 4,862,886 A | 9/1989 | Clarke et al. | |
| 4,878,492 A | 11/1989 | Sinofsky et al. | |
| 4,966,596 A | 10/1990 | Kuntz et al. | |
| 4,993,412 A | 2/1991 | Murphy-Chutorian | |
| 5,010,886 A | 4/1991 | Passafaro et al. | |
| 5,026,366 A | 6/1991 | Leckrone | |
| 5,026,367 A | 6/1991 | Leckrone et al. | |
| 5,029,588 A | 7/1991 | Yock et al. | |
| 5,041,108 A | 8/1991 | Fox et al. | |
| 5,053,033 A | 10/1991 | Clarke | |
| 5,055,109 A | 10/1991 | Gould et al. | |
| 5,176,674 A | 1/1993 | Hofmann | |
| 5,192,278 A | 3/1993 | Hayes et al. | |
| 5,281,212 A | 1/1994 | Savage et al. | |
| 5,304,171 A | 4/1994 | Gregory et al. | |
| 5,334,207 A | 8/1994 | Gay et al. | |
| 5,350,375 A | 9/1994 | Deckelbaum et al. | |
| 5,354,324 A | 10/1994 | Gregory | |
| 5,395,361 A | 3/1995 | Fox et al. | |
| 5,423,805 A | 6/1995 | Brucker et al. | |
| 5,439,446 A * | 8/1995 | Barry .................... | A61F 2/958 604/103.01 |
| 5,468,239 A | 11/1995 | Tanner et al. | |
| 5,470,330 A | 11/1995 | Goldenberg et al. | |
| 5,573,531 A | 11/1996 | Gregory | |
| 5,649,923 A | 7/1997 | Gregory et al. | |
| 5,722,972 A | 3/1998 | Power et al. | |
| 5,722,979 A | 3/1998 | Kusleika | |
| 5,733,301 A | 3/1998 | Forman | |
| 5,741,246 A | 4/1998 | Prescott | |
| 5,769,843 A | 6/1998 | Abela et al. | |
| 5,876,373 A | 3/1999 | Giba et al. | |
| 5,876,397 A | 3/1999 | Edelman et al. | |
| 5,944,687 A | 8/1999 | Benett et al. | |
| 6,022,309 A | 2/2000 | Celliers et al. | |
| 6,024,738 A | 2/2000 | Daikuzono et al. | |
| 6,123,718 A | 9/2000 | Tu et al. | |
| 6,132,423 A | 10/2000 | Aita et al. | |
| 6,210,404 B1 | 4/2001 | Shadduck | |
| 6,283,958 B1 | 9/2001 | Vogl et al. | |
| 6,379,325 B1 | 4/2002 | Benett et al. | |
| 6,551,302 B1 | 4/2003 | Rosinko et al. | |
| 6,561,998 B1 | 5/2003 | Roth et al. | |
| 6,592,612 B1 | 7/2003 | Samson et al. | |
| 6,660,001 B2 | 12/2003 | Gregory | |
| 6,752,800 B1 | 6/2004 | Winston et al. | |
| 7,125,404 B2 | 10/2006 | Levatter | |
| 7,144,248 B2 | 12/2006 | Irwin | |
| 7,226,470 B2 | 6/2007 | Kemény et al. | |
| 7,238,178 B2 | 7/2007 | Maschke | |
| 7,306,585 B2 | 12/2007 | Ross | |
| 7,818,053 B2 | 10/2010 | Kassab | |
| 7,891,361 B2 | 2/2011 | Irwin | |
| 8,104,483 B2 | 1/2012 | Taylor | |
| 8,162,964 B2 | 4/2012 | Piippo et al. | |
| 8,167,810 B2 | 5/2012 | Maschke | |
| 8,396,548 B2 | 3/2013 | Perry | |
| 8,454,669 B2 | 6/2013 | Irwin | |
| 8,465,452 B2 | 6/2013 | Kassab | |
| 8,551,096 B2 | 10/2013 | Perry et al. | |
| 8,574,247 B2 | 11/2013 | Adams et al. | |
| 8,684,970 B1 | 4/2014 | Koyfman et al. | |
| 8,702,773 B2 | 4/2014 | Keeler | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,790,386 B2 | 7/2014 | Dwork | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,138,249 B2 | 9/2015 | Adams et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,320,530 B2 | 4/2016 | Grace | |
| 2001/0027310 A1 | 10/2001 | Parisi et al. | |
| 2002/0151880 A1 * | 10/2002 | Lafontaine ............. | A61B 18/02 606/21 |
| 2003/0009157 A1 | 1/2003 | Levine | |
| 2003/0181938 A1 | 9/2003 | Roth et al. | |
| 2003/0229370 A1 | 12/2003 | Miller | |
| 2004/0143287 A1 | 7/2004 | Konstantino | |
| 2005/0021071 A1 | 1/2005 | Konstantino | |
| 2005/0183729 A1 * | 8/2005 | Fischer, Jr. ........ | A61M 16/0472 128/207.29 |
| 2005/0216044 A1 | 9/2005 | Hong | |
| 2005/0240212 A1 | 10/2005 | McAuley | |
| 2005/0251116 A1 | 11/2005 | Steinke et al. | |
| 2006/0189930 A1 | 8/2006 | Lary et al. | |
| 2006/0190022 A1 | 8/2006 | Beyar et al. | |
| 2006/0271154 A1 * | 11/2006 | Woodall ........... | A61B 17/12136 623/1.11 |
| 2007/0078500 A1 | 4/2007 | Ryan et al. | |
| 2007/0093745 A1 | 4/2007 | Steward et al. | |
| 2007/0198047 A1 | 8/2007 | Schon et al. | |
| 2008/0103575 A1 | 5/2008 | Gerber | |
| 2008/0249515 A1 | 10/2008 | Taylor | |
| 2009/0112198 A1 | 4/2009 | Khanna et al. | |
| 2009/0112239 A1 | 4/2009 | To | |
| 2009/0270846 A1 | 10/2009 | Okada et al. | |
| 2009/0270850 A1 | 10/2009 | Zhou et al. | |
| 2010/0016862 A1 | 1/2010 | Hawkins et al. | |
| 2010/0049182 A1 | 2/2010 | Ryan et al. | |
| 2010/0152720 A1 | 6/2010 | Sauro et al. | |
| 2010/0222786 A1 | 9/2010 | Kassab | |
| 2011/0152683 A1 | 6/2011 | Gerrans et al. | |
| 2011/0190751 A1 * | 8/2011 | Ingle .................... | A61B 18/02 606/21 |
| 2011/0208185 A1 | 8/2011 | Diamant et al. | |
| 2012/0116289 A1 | 5/2012 | Hawkins et al. | |
| 2012/0203255 A1 | 8/2012 | Hawkins et al. | |
| 2012/0221013 A1 | 8/2012 | Hawkins | |
| 2012/0303011 A1 | 11/2012 | Schaeffer | |
| 2013/0030431 A1 | 1/2013 | Adams | |
| 2013/0030447 A1 | 1/2013 | Adams | |
| 2013/0046293 A1 | 2/2013 | Arai et al. | |
| 2013/0096545 A1 | 4/2013 | Laudenslager et al. | |
| 2013/0197555 A1 | 8/2013 | Schaer | |
| 2014/0005576 A1 | 1/2014 | Adams et al. | |
| 2014/0039513 A1 | 2/2014 | Hakala | |
| 2014/0046229 A1 | 2/2014 | Hawkins et al. | |
| 2014/0046353 A1 | 2/2014 | Adams | |
| 2014/0052114 A1 | 2/2014 | Ben-Oren et al. | |

(56) References Cited

U.S. PATENT DOCUMENTS

| | | |
|---|---|---|
| 2014/0052145 A1 | 2/2014 | Adams et al. |
| 2014/0074113 A1 | 3/2014 | Hakala et al. |
| 2014/0133814 A1 | 5/2014 | Stevens |
| 2014/0163592 A1 | 6/2014 | Hawkins et al. |
| 2014/0214061 A1 | 7/2014 | Adams |
| 2014/0276682 A1 | 9/2014 | Hendrick et al. |
| 2014/0288570 A1 | 9/2014 | Adams |
| 2015/0039002 A1 | 2/2015 | Hawkins |
| 2015/0073430 A1 | 3/2015 | Hakala et al. |
| 2015/0105714 A1 | 4/2015 | Laudenslager et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0184022 A1 | 6/2016 | Grace et al. |
| 2016/0184023 A1 | 6/2016 | Grace et al. |
| 2016/0262784 A1 | 9/2016 | Grace et al. |
| 2017/0265942 A1 | 9/2017 | Grace et al. |
| 2017/0333132 A1 | 11/2017 | Grace et al. |
| 2018/0008348 A1 | 1/2018 | Grace et al. |

FOREIGN PATENT DOCUMENTS

| | | |
|---|---|---|
| DE | 4240182 C2 | 6/1994 |
| DE | 4437578 A1 | 5/1996 |
| EP | 0182689 B1 | 5/1986 |
| EP | 0189329 A2 | 7/1986 |
| EP | 0355200 A1 | 2/1990 |
| EP | 0820786 A2 | 1/1998 |
| EP | 0902654 B1 | 3/1999 |
| EP | 1200002 B1 | 5/2002 |
| JP | H01148278 A | 6/1989 |
| JP | 2004215862 A | 8/2004 |
| JP | 2009061083 A | 3/2009 |
| KR | 100996733 B1 | 11/2010 |
| WO | WO199006087 A | 6/1990 |
| WO | 1991010403 A1 | 7/1991 |
| WO | WO199745157 A | 12/1997 |
| WO | WO2000012168 A1 | 3/2000 |
| WO | 2003057060 A1 | 7/2003 |
| WO | WO2004060460 A2 | 7/2004 |
| WO | 2006006169 A2 | 1/2006 |
| WO | 2010054048 A2 | 5/2010 |
| WO | 2009152352 A2 | 12/2010 |
| WO | 2011006017 A1 | 1/2011 |
| WO | 2013070750 A1 | 5/2013 |
| WO | 2013169807 A1 | 11/2013 |
| WO | 2014004887 A1 | 1/2014 |
| WO | 2014025397 A1 | 2/2014 |
| WO | 2014025620 A1 | 2/2014 |
| WO | 2014025981 A1 | 2/2014 |
| WO | 2014028885 A1 | 2/2014 |
| WO | 2014043400 A1 | 3/2014 |
| WO | 2014163955 A1 | 10/2014 |
| WO | 2015017499 A1 | 2/2015 |
| WO | 2015034840 A1 | 5/2015 |
| WO | 2015171515 A1 | 11/2015 |

OTHER PUBLICATIONS

International Search Report and Written Opinion issued in PCT/US2015/068169, dated May 13, 2016, 28 pages.

International Search Report and Written Opinion issued in PCT/US2015/068170, dated May 13, 2016, 13 pages.

Supplemental European Search Report issued in EP Application 14778867, dated Aug. 10, 2016, 7 pages.

International Preliminary Report on Patentability issued in PCT/US2015/068161, dated Jul. 13, 2017, 15 pages.

International Search Report and Written Opinion issued in PCT/US2015/068169, dated Jul. 13, 2017, 21 pages.

International Search Report and Written Opinion issued in PCT/US2017/043680, dated Oct. 31, 2017, 14 pages.

International Search Report and Written Opinion issued in PCT/US2017/043762, dated Oct. 31, 2017, 14 pages.

International Preliminary Report on Patentability issued in PCT/US2014/019268, dated Sep. 24, 2015, 9 pages.

International Search Report and Written Opinion issued in PCT/US2014/019268 dated Jun. 13, 2014, 13 pages.

International Search Report and Written Opinion issued in PCT/US2015/068173, dated Apr. 19, 2016, 16 pages.

U.S. Appl. No. 14/984,050 entitled Laser-Induced Fluid Filled Balloon Catheter, filed Dec. 30, 2015.

U.S. Appl. No. 14/984,308 entitled Laser-Induced Pressure Wave Emitting Catheter Sheath, filed Dec. 30, 2015.

U.S. Appl. No. 14/984,710 entitled Electrically-Induced Pressure Wave Emitting Catheter Sheath, filed Dec. 30, 2015.

U.S. Appl. No. 15/090,736 entitled "Apparatus and Method for Balloon Angioplasty," filed Apr. 5, 2016.

* cited by examiner

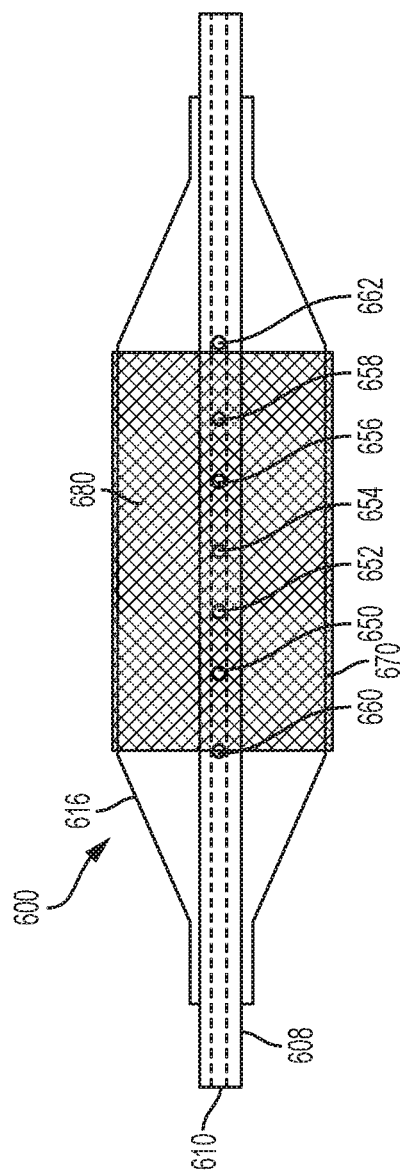

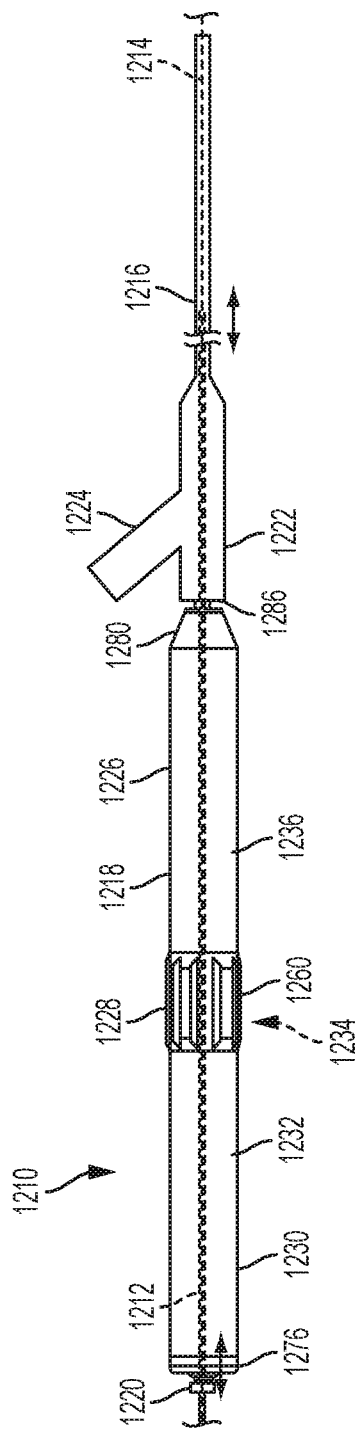
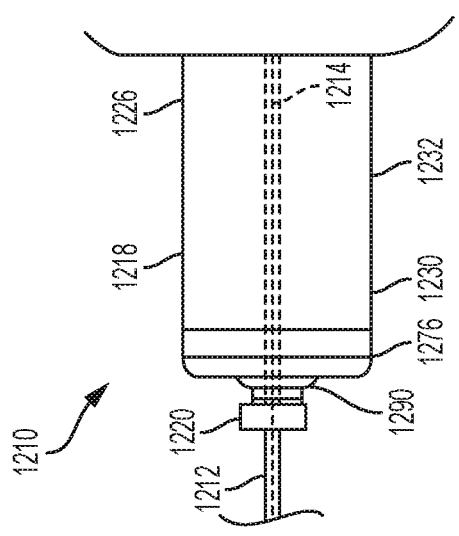
FIG. 12A
FIG. 12B

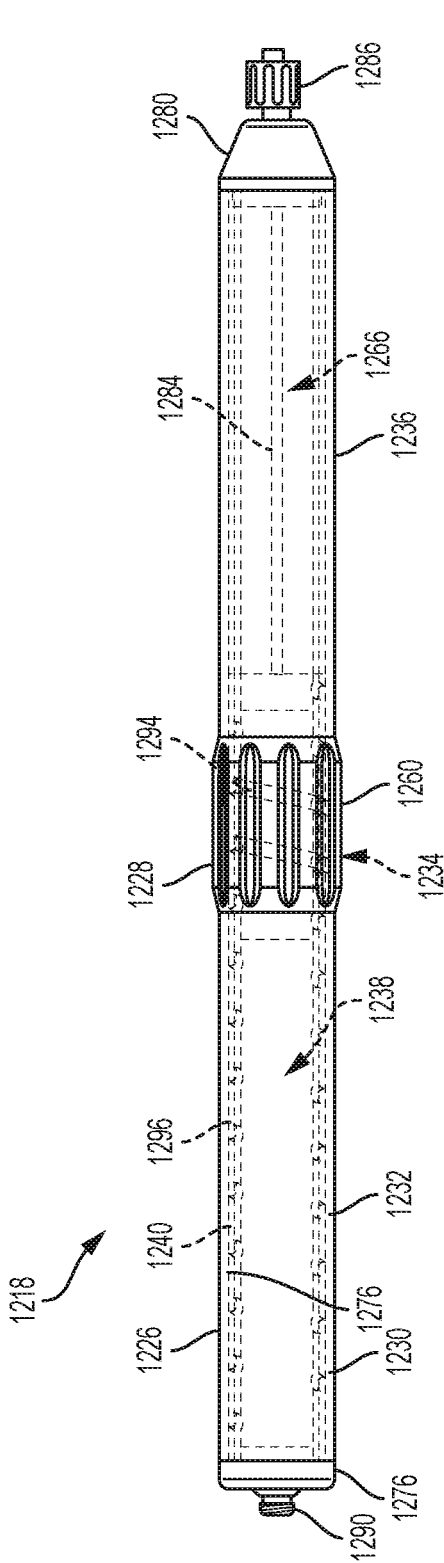
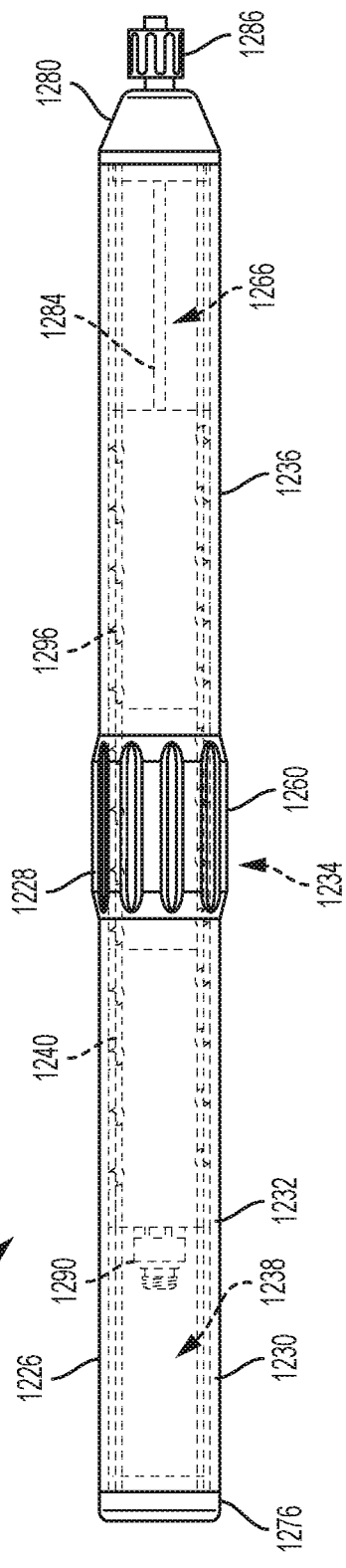
FIG. 13C
FIG. 13D

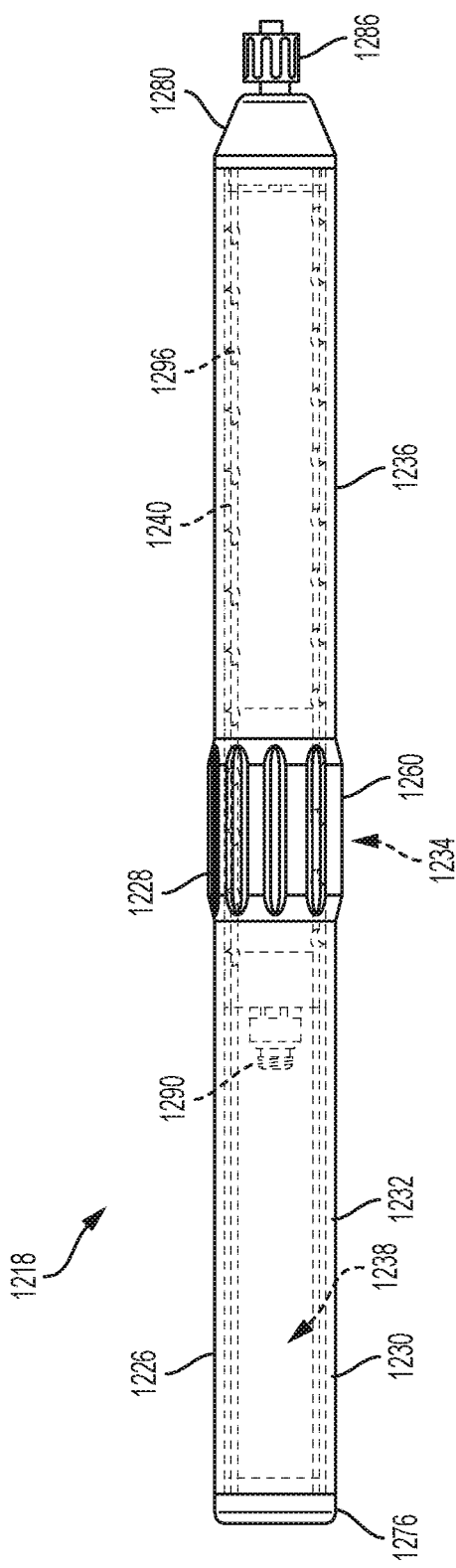
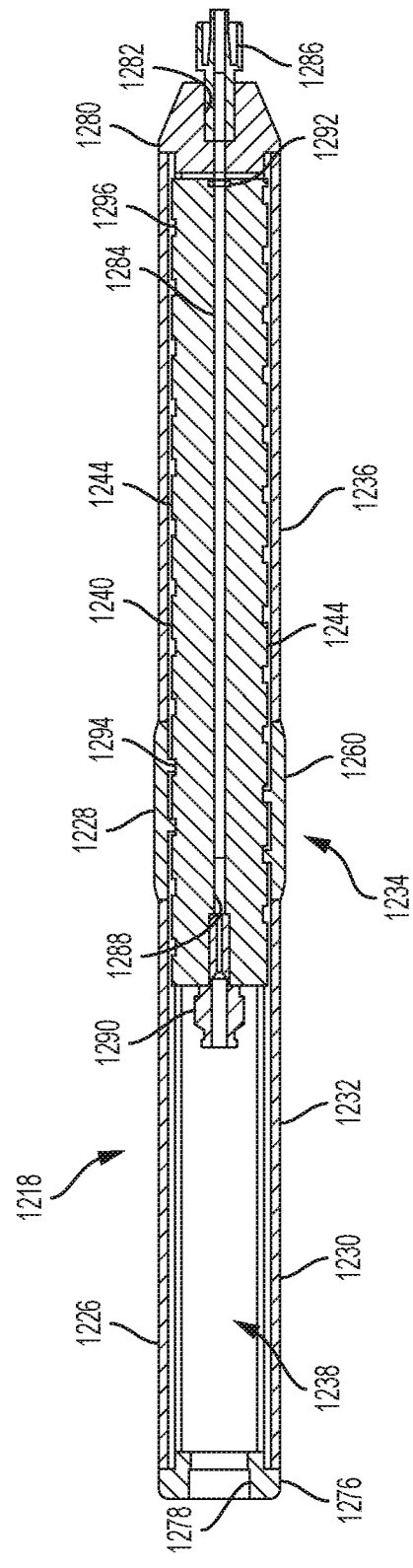
FIG. 13E
FIG. 13F

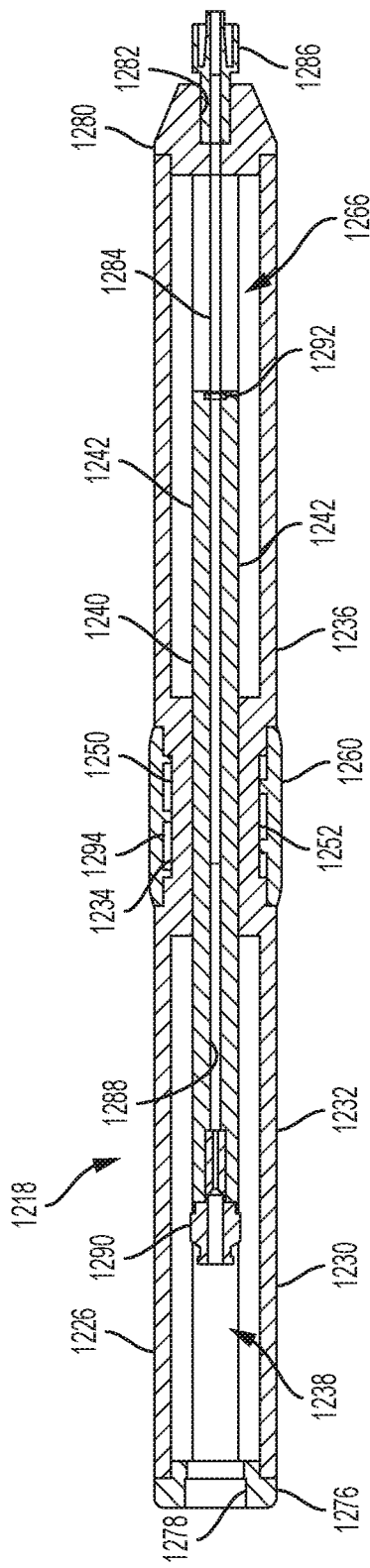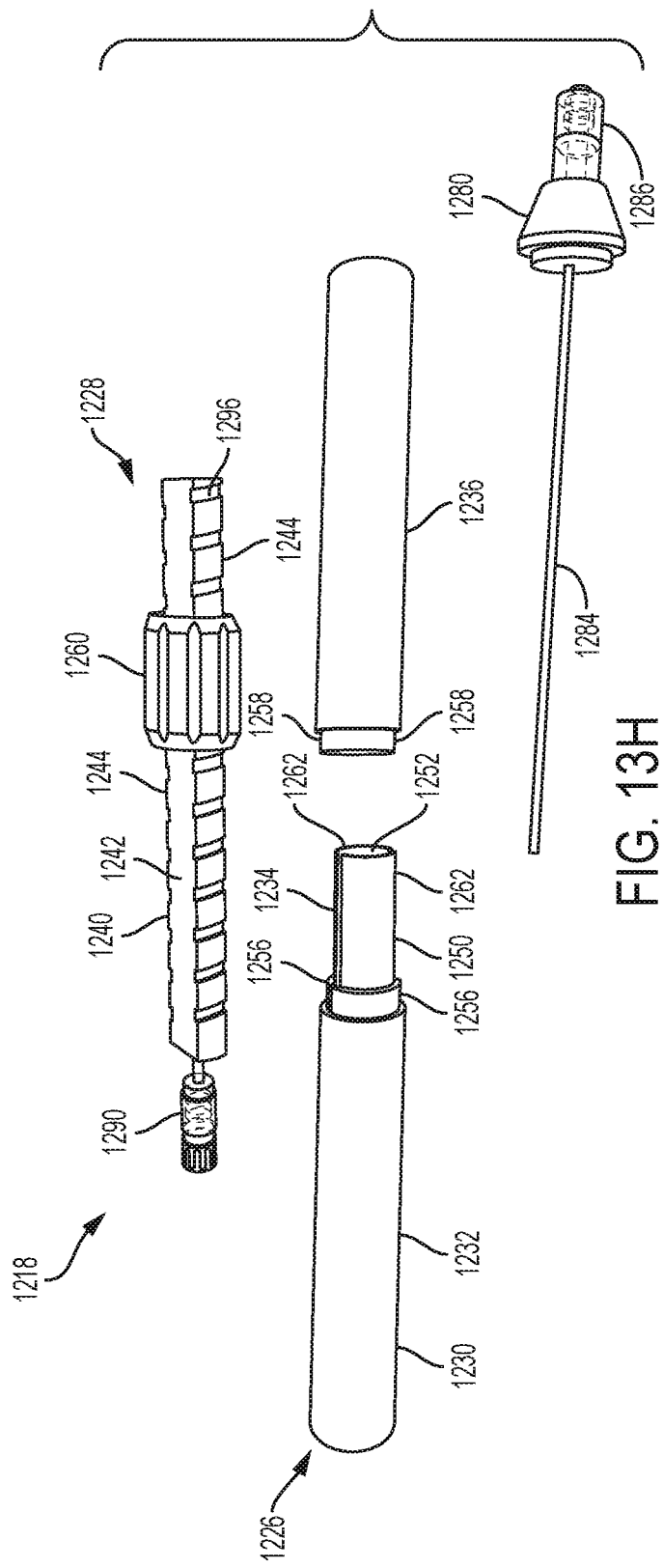
FIG. 13G
FIG. 13H

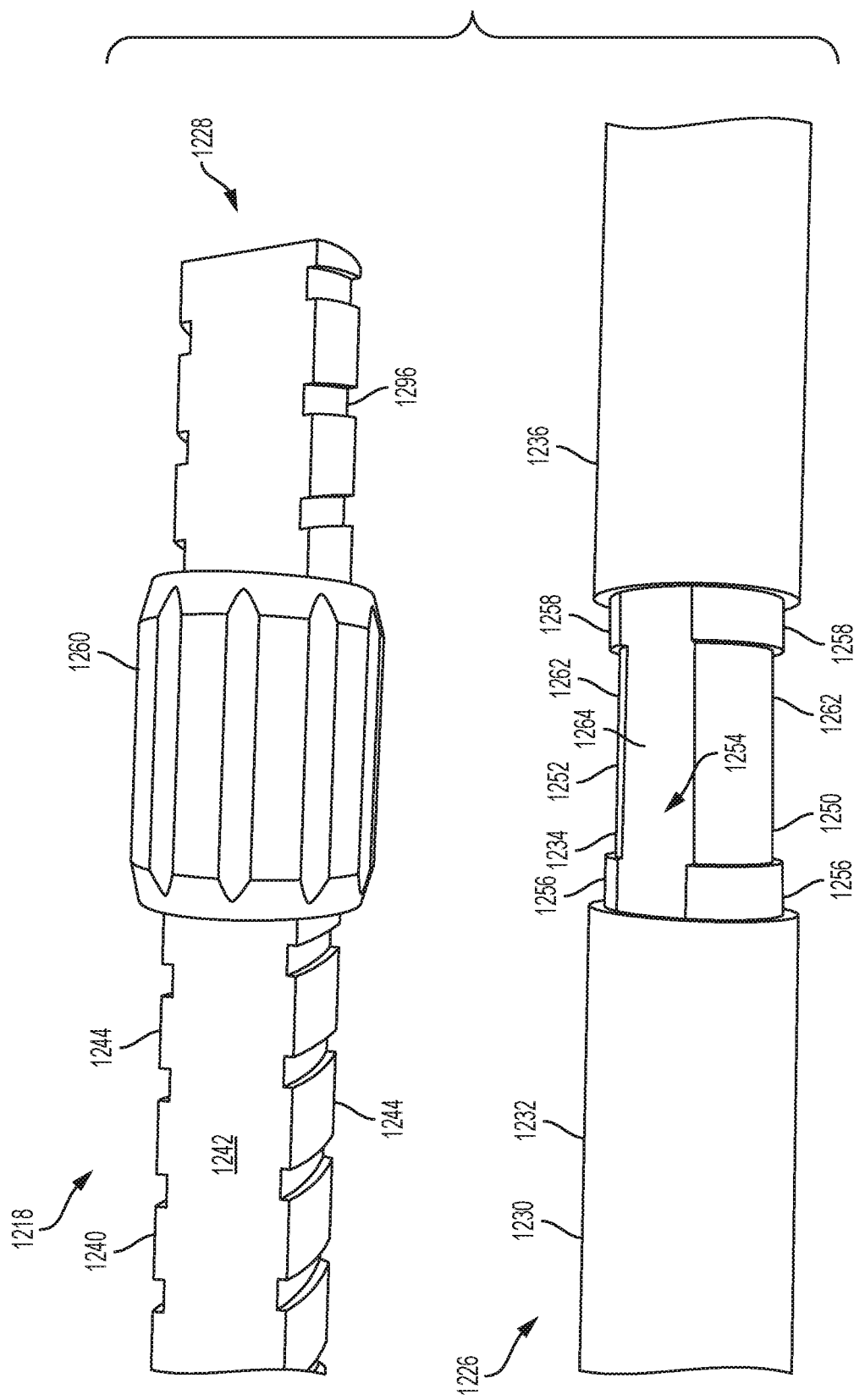

ELECTRICALLY-INDUCED FLUID FILLED BALLOON CATHETER

CROSS REFERENCE TO RELATED APPLICATIONS

The present application claims the benefit of and priority, under 35 U.S.C. § 119(e), to commonly assigned, U.S. Application Ser. No. 62/098,242, filed on Dec. 30, 2014 which is hereby incorporated herein by reference in its entirety for all that it teaches and for all purposes. The present application claims the benefit of and priority, under 35 U.S.C. § 119(e), to commonly assigned, U.S. Application Ser. No. 62/209,691, filed on Aug. 25, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/232,318, filed on Sep. 24, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/248,875, filed on Oct. 30, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/248,913, filed on Oct. 30, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/257,404, filed on Nov. 19, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/261,085, filed on Nov. 30, 2015 which is hereby incorporated herein by reference in its entirety for all that it teaches and for all purposes.

FIELD

The present disclosure relates generally to the use of medical devices for the treatment of vascular conditions. In particular, the present disclosure provides materials and methods for using electrically-induced pressure waves to disrupt vascular blockages and to deliver therapeutic agents to the blockage area.

BACKGROUND

Coronary artery disease (CAD) is the most common form of heart disease, affecting millions of people. Peripheral artery disease (PAD) also affects millions of people. CAD and PAD most often results from a condition known as atherosclerosis, which generally manifests as the accumulation of a waxy substance on the inside of a subject's arteries. This substance, called plaque, is made of cholesterol, fatty compounds, calcium, and a blood-clotting material called fibrin.

As the plaque builds up, the coronary and peripheral arteries narrows, or becomes stenotic, making it more difficult for blood to flow to the heart. As the blockage worsens in a person's coronary arteries, blood flow to the heart slows, and a condition called angina pectoris, or simply angina, may develop. Angina is like a squeezing, suffocating, or burning feeling in the chest. The pain typically develops when the heart requires additional blood, such as during exercise or times of emotional stress. In time, a narrowed or blocked artery can lead to a heart attack. A number of medicines can be used to relieve the angina pain that comes with CAD, but these medicines cannot clear blocked arteries. A moderate to severely narrowed coronary artery may need more aggressive treatment to reduce the risk of a heart attack. As the plaque builds up in peripheral arteries, the artery narrows, or becomes stenotic, thereby making it more difficult for blood to flow through the peripheral arteries. The reduced blood flow in the peripheral arteries limits the amount of oxygen that is delivered to the extremities, which in turn may cause pain in the extremities and, in severe cases, gangrene, which may ultimately require amputation.

Balloon angioplasty and other transluminal medical treatments are well-known and have been proven efficacious in the treatment of stenotic lesions at the core of CAD and/or PAD. In a typical angioplasty procedure, a catheter is inserted into the groin or arm of a subject and guided to the affected arteries, such as the aorta and into the coronary arteries of the heart when treating CAD and the peripheral arteries when treating PAD. There, blocked arteries can be opened with a balloon positioned at the tip of the catheter. Initially, angioplasty was performed only with balloon catheters, but technical advances have been made and improved patient outcomes have been achieved with the placement of small metallic spring-like devices called "stents" at the site of the blockage. The implanted stent serves as a scaffold that keeps the artery open. Angioplasty and stenting techniques are widely used around the world and provide an alternative option to bypass surgery for improving blood flow to the heart muscle. There are, however, limitations associated with angioplasty and stenting, one of which is called "restenosis."

Restenosis occurs when the treated vessel becomes blocked again. For example, when a stent is placed in a blood vessel, new tissue grows inside the stent, covering the struts of the stent. Initially, this new tissue consists of healthy cells from the lining of the arterial wall (such as, endothelium). This is a favorable effect because development of normal lining over the stent allows blood to flow smoothly over the stented area without clotting. Later, scar tissue may form underneath the new healthy lining. However, in about 25 percent of patients, the growth of scar tissue underneath the lining of the artery may be so thick that it can obstruct the blood flow and produce another blockage. "In-stent" restenosis is typically seen 3 to 6 months after the initial procedure. Another significant limitation of the use of stents is stent thrombosis, which, although rare (occurring in only 1 percent of patients), most commonly presents as acute myocardial infarction.

In addition to angioplasty and the deployment of stents, other types of intervention for stenotic vessels include atherectomy, bypass surgery, and the use of laser ablation and mechanical cutting systems to reduce the plaque size. Treatments using various pharmacological agents have also been developed, including medical infusions, drug-eluding stents (DES), and drug eluting balloons (DEB). Given the persistence of CAD and PAD, however, the most efficacious means for improving therapeutic outcomes may involve combinations of therapies designed not only to reduce plaque size in the short term, but also to prevent future complications such as restenosis. Combinatorial therapies may offer the best chance to improve therapeutic outcomes for people suffering from CAD and PAD.

SUMMARY

These and other needs are addressed by the various aspects, embodiments, and configurations of the present disclosure.

The present disclosure provides a method for treating an obstruction within vasculature of a subject, the method comprising positioning a catheter within vasculature of a subject, the catheter comprising a sheath having a lumen, a proximal end and a distal end, a balloon assembly circumferentially arranged around a portion of the sheath, wherein at least a portion of the balloon assembly is coated with one or more therapeutic agents, at least one electrode assembly coupled to the sheath and disposed within the balloon assembly, wherein the at least one electrode assembly is disposed proximate the distal end of the sheath, and one or more liquid medium ports disposed about the sheath and within the balloon assembly, positioning the balloon assembly adjacent an obstruction within the vasculature, inflating the balloon assembly by delivering a liquid medium through an inner lumen of the catheter and out one or more liquid medium ports into the balloon assembly until a desired inflation pressure is obtained, and activating the at least one electrode assembly within the balloon assembly to produce at least one pulse of electrical energy across the electrode assembly, whereupon the electrical energy reacts with the liquid medium and generates one or more propagating pressure waves that delivers the one or more therapeutic agents to the vascular obstruction or to the tissues surrounding the vascular obstruction.

A method according to the previous paragraph, wherein the plurality of propagating pressure waves enhances the penetration of the one or more therapeutic agents into the vascular obstruction or into the tissues surrounding the vascular obstruction.

A method according to any of the two previous paragraphs, wherein the liquid medium is any one of iodine-containing contrast medium or gadolinium contrast medium.

A method according to any of the three previous paragraphs, wherein the liquid medium is delivered into the balloon assembly to create a pressure greater than 0.0 atmospheres to about 20.0 atmospheres within the balloon assembly.

A method according to any of the four previous paragraphs, wherein the one or more therapeutic agents comprises one or more oxidation-insensitive drugs in a polymer-free drug preparation.

A method according to any of the five previous paragraphs, wherein the one or more oxidation-insensitive drugs is one or more of taxanes, thalidomide, statins, corticoids, and lipophilic derivatives of corticoids.

The present disclosure provides a catheter comprising a sheath having a guidewire lumen, an inflation lumen, a proximal end and a distal end, at least one electrode assembly adjacent to the guidewire lumen, a balloon assembly circumferentially arranged around a portion of the sheath, means for directing electrical energy produced by the electrode assembly towards the guidewire lumen or a guidewire within the guidewire lumen, and one or more liquid medium ports disposed within the sheath and within the balloon assembly.

A catheter according to the previous paragraph, wherein the means for directing electrical energy produced by the electrode assembly towards the guidewire lumen or a guidewire within the guidewire lumen comprises a deflector.

A catheter according to any of the two previous paragraphs, wherein the electrode assembly is oriented to direct energy at the deflector, wherein the deflector subsequently directs the energy at the guidewire lumen or a guidewire.

A catheter according to any of the three previous paragraphs, wherein the liquid medium is contrast medium or contrast solution.

The present disclosure also provides a method treating an obstruction within vasculature of a subject, the method comprising positioning a catheter within vasculature of a subject, the catheter comprising a sheath having a guidewire lumen, an inflation lumen, a proximal end and a distal end, at least one electrode assembly, a balloon assembly circumferentially arranged around a portion of the sheath and the at least one electrode assembly, means for directing electrical energy produced by the at least one electrode assembly towards the guidewire lumen or a guidewire within the guidewire lumen, and one or more liquid medium ports disposed within the sheath and within the balloon assembly, positioning the balloon assembly adjacent an obstruction within the vasculature, inflating the balloon assembly by delivering a liquid medium through the inflation lumen and out one or more liquid medium ports into the balloon assembly until a desired inflation pressure is obtained, and activating the at least one electrode assembly within the balloon assembly to produce at least one pulse of electrical energy from the electrode assembly, whereupon the electrical energy reacts with the liquid medium and generates one or more propagating pressure waves that cause the balloon assembly to engage and disrupt at least a portion of the vascular obstruction, and wherein the means for directing electrical energy produced by the electrode assembly towards the guidewire lumen or a guidewire within the guidewire lumen induces vibrations within the guidewire.

A method according to the previous paragraph, wherein the means for directing electrical energy produced by the electrode assembly towards the guidewire lumen or a guidewire within the guidewire lumen comprises an outer band coupled to the distal end of the sheath, wherein the outer band comprises a distal end, and the electrode assembly is disposed proximate the distal end of the outer band.

A method according to any of the two previous paragraphs, wherein the electrode assembly is directed at the guidewire lumen or a guidewire.

The present disclosure also provides a system comprising a catheter comprising a sheath having a first lumen, an inflation lumen, a proximal end and a distal end, a sealable valve having a guidewire lumen and a seal, a balloon having a proximal end and distal end, wherein the proximal end of the balloon is coupled to the distal end of the sheath, wherein the distal end of the balloon is coupled to the sealable valve, and whereupon introducing a guidewire into the first lumen and the guidewire lumen and introducing inflation fluid through the inflation lumen and into the balloon, the inflation fluid actuates the seal within the valve and closes an opening between the valve and the guidewire, and an electrode catheter comprising a proximal portion, distal portion, at least one electrode assembly, wherein the proximal portion is coupled to an electrical generator, wherein the at least one electrode assembly is coupled to the electrical generator, wherein the at least one electrode assembly is disposed within the balloon.

The present disclosure also provides a method for treating an obstruction within vasculature of a subject, the method comprising positioning a guidewire within vasculature of a subject, positioning a catheter within the vasculature of a subject over the guidewire, the catheter comprising a sheath having a first guidewire lumen, an inflation lumen, a proximal end and a distal end, a sealable valve having a second guidewire lumen and a seal, wherein the guidewire is inserted through the first guidewire lumen an the second guidewire lumen, a balloon having a proximal end and distal end, wherein the proximal end of the balloon is coupled to the distal end of the sheath, wherein the distal end of the balloon is coupled to the sealable valve, positioning the balloon adjacent an obstruction within the vasculature, inflating the balloon by delivering a liquid medium through the inflation lumen into the balloon until a desired inflation pressure is obtained whereupon delivering the inflation fluid into the balloon, the inflation fluid actuates the seal within the valve and closes an opening between the valve and the guidewire, and introducing at least one electrode assembly into the balloon, activating the at least one electrode assembly within the balloon to produce at least one pulse of electrical energy from the electrode assembly, whereupon the electrical energy reacts with the liquid medium and generates one or more pressure waves that propagate through the balloon and disrupt at least a portion of the vascular obstruction.

A method according to the previous paragraph, wherein the inflation fluid is contrast medium or contrast solution.

A method according to any of the two previous paragraphs, wherein the inflation fluid is any one of iodine-containing contrast medium or gadolinium contrast medium.

The present disclosure also provides a catheter comprising a sheath having a guidewire lumen, an inflation lumen, a proximal end and a distal end, at least one electrode assembly adjacent to the guidewire lumen, wherein the at least one electrode assembly is coupled to an electrical generator and produces an electrical pulse, a balloon assembly circumferentially arranged around a portion of the sheath and around at least one electrode assembly, one or more liquid medium ports disposed within the sheath and within the balloon assembly, and a pressure-wave reflective element disposed adjacent the balloon assembly, wherein the pressure-wave reflective element attenuates the pressure wave passing therethrough upon creation of the pressure wave within the balloon assembly by the reaction between the electrical pulse produced by the electrode assembly and a liquid medium introduced into the balloon assembly via the one or more liquid medium ports.

A catheter according to the previous paragraph, wherein the pressure-wave reflective element is integrally disposed within the balloon assembly.

A catheter according to any of the two previous paragraphs, wherein the balloon assembly has an exterior, and wherein the pressure-wave reflective element is disposed on the exterior of the balloon assembly.

A catheter according to any of the three previous paragraphs, wherein the balloon assembly has an interior, and wherein the pressure-wave reflective element is disposed on the interior of the balloon assembly.

A catheter according to any of the four previous paragraphs, wherein the pressure-wave reflective element comprises a plurality of openings.

A catheter according to any of the five previous paragraphs, wherein the plurality of openings are between 100 and 900 microns.

A catheter according to any of the six previous paragraphs, wherein a percentage of the openings within an area of a portion of the pressure-wave reflective element is between 10 percent and 90 percent.

A catheter according to any of the seven previous paragraphs, wherein an area of the pressure-wave reflective element comprises the openings and a structural mass, wherein a ratio of the openings to the structural mass within the area is between 1:1 and 1:10.

A catheter according to any of the eight previous paragraphs, wherein the plurality of openings comprise at least one of the following shapes: circle; oval; triangle; square; rectangle; polygon; diamond; pentagon; hexagon; heptagon; octagon; nonagon; and decagon.

A catheter according to any of the nine previous paragraphs, wherein the liquid medium is contrast medium or contrast solution.

A catheter according to any of the ten previous paragraphs, wherein the liquid medium is any one of iodine-containing contrast medium or gadolinium contrast medium.

The present disclosure also provides a method for treating an obstruction within vasculature of a subject, the method comprising positioning a catheter within vasculature of a subject, the catheter comprising a sheath having a guidewire lumen, an inflation lumen, a proximal end and a distal end, at least one electrode assembly adjacent to the guidewire lumen, wherein the at least one electrode assembly is coupled to an electrical generator and produces an electrical pulse, a balloon assembly circumferentially arranged around a portion of the sheath and around at least one electrode assembly, one or more liquid medium ports disposed within the sheath and within the balloon assembly, and a pressure-wave reflective element disposed adjacent the balloon assembly, positioning the balloon assembly adjacent an obstruction within the vasculature, inflating the balloon assembly by delivering a liquid medium through the inflation lumen and out one or more liquid medium ports into the balloon assembly until a desired inflation pressure is obtained, and activating the at least one electrode assembly within the balloon to produce at least one pulse of electrical energy from the electrode assembly, whereupon the electrical energy reacts with the liquid medium and generates one or more pressure waves that propagate through the balloon and disrupt at least a portion of the vascular obstruction, wherein the pressure-wave reflective element attenuates the pressure wave passing through the balloon assembly.

A method according to the previous paragraph, wherein the pressure-wave reflective element comprises a plurality of openings.

A method according to any of the two previous paragraphs, wherein the plurality of openings are between 100 and 900 microns.

A method according to any of the three previous paragraphs, wherein a percentage of the openings within an area of a portion of the pressure-wave reflective element is between 10 percent and 90 percent.

A method according to any of the four previous paragraphs, wherein an area of the pressure-wave reflective element comprises the openings and a structural mass, wherein a ratio of the openings to the structural mass within the area is between 1:1 and 1:10.

A method according to any of the five previous paragraphs, wherein the plurality of openings comprise at least one of the following shapes: circle; oval; triangle; square; rectangle; polygon; diamond; pentagon; hexagon; heptagon; octagon; nonagon; and decagon.

A method according to any of the six previous paragraphs, further comprising the step of re-positioning the balloon assembly such that the balloon is adjacent another portion of the obstruction.

A method according to any of the seven previous paragraphs, further comprising the step of moving the at least one electrode assembly within the balloon assembly.

A method according to any of the eight previous paragraphs, wherein the within the at least one electrode assembly is re-positioned within the pressure-wave reflective element.

A method according to any of the nine previous paragraphs, further comprising the step of re-positioning at least one electrode assembly within the balloon assembly.

A method according to any of the ten previous paragraphs, wherein the within the at least one electrode assembly is re-positioned within the pressure-wave reflective element.

A method according to any of the eleven previous paragraphs, further comprising the steps of removing the catheter from the vasculature.

A method according to any of the twelve previous paragraphs, further comprising the step of inserting a drug-coated balloon into the vasculature such that the drug-coated balloon is disposed adjacent a remaining portion of the occlusion.

A method according to any of the thirteen previous paragraphs, further comprising the step of inflating the drug-coated balloon and applying a drug disposed on the drug-coated balloon to the remaining portion of the occlusion.

The present disclosure also provides a catheter system comprising a balloon catheter comprising a sheath having a proximal end and a distal end and a lumen therein, and a balloon coupled to the sheath, an electrode catheter comprising a proximal end capable of coupling to the high generator, a distal end, and at least one electrode assembly coupled to the sheath, wherein the electrode catheter is disposed within the sheath and the balloon, a means for introducing a liquid medium into the cavity, a handle comprising a base coupled to the proximal end of the sheath, and a drive mechanism translatably coupled to the base, the drive mechanism coupled to the electrode catheter such that translation of the drive mechanism relative to the base causes translation of the electrode catheter within the lumen of the sheath and within the balloon.

A catheter system according to the previous paragraph, wherein the drive mechanism comprises a control element movably coupled to the base, and a coupling translatably coupled to the base and driven by the control element, the coupling coupled to the electrode catheter such that movement of the control element relative to the base causes translation of the electrode catheter within the lumen of the sheath and within the balloon.

A catheter system according to any of the two previous paragraphs, wherein the control element is rotatably coupled to the base, and rotation of the control element relative to the base causes translation of the electrode catheter within the lumen of the sheath and within the balloon.

A catheter system according to any of the three previous paragraphs, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the electrode catheter within the lumen of the sheath and within the balloon.

A catheter system according to any of the four previous paragraphs, wherein the handle further comprises a tube coupled to the base, the tube receiving the electrode catheter, and wherein the shaft includes an inner lumen that translatably receives the tube as the shaft translates within the base.

A catheter system according to any of the five previous paragraphs, wherein the drive mechanism further comprises a seal coupled to the shaft, the seal translatably engaging the tube.

A catheter system according to any of the six previous paragraphs, wherein the tube is a hypotube.

A catheter system according to any of the seven previous paragraphs, wherein the base includes a first key feature, the shaft includes a second key feature that couples to the first key feature to inhibit rotation of the shaft relative to the base.

A catheter system according to any of the eight previous paragraphs, wherein the base includes an opening disposed within the control element, the second threaded surface extending through the opening to couple to the first threaded surface.

The present disclosure also provides a method for treating an obstruction within vasculature of a subject, the method comprising positioning a catheter system within vasculature of a subject, the catheter system comprising a balloon catheter comprising a sheath having a proximal end and a distal end and a lumen therein, and a balloon coupled to the sheath, an electrode catheter comprising a proximal end capable of coupling to the high voltage pulse generator, a distal end, and at least one electrode assemblies, wherein the catheter is disposed within the sheath and the balloon, a means for introducing a liquid medium into the cavity, a handle comprising a base coupled to the proximal end of the sheath, and a drive mechanism translatably coupled to the base, the drive mechanism coupled to the electrode catheter such that translation of the drive mechanism relative to the base causes translation of the electrode catheter within the lumen of the sheath and within the balloon, positioning the balloon adjacent an obstruction within the vasculature, inflating the balloon by delivering a liquid medium into the balloon until a desired inflation pressure is obtained, activating the at least one electrode assembly within the balloon to produce one or more pulses of electrical energy from the at least electrical assembly, wherein producing the one or more pulses of electrical energy from the at least electrode assembly reacts with the liquid medium and generates a plurality of propagating pressure waves that cause the balloon assembly to engage and disrupt at least a portion of the vascular obstruction, and actuating the handle and sliding the at least electrode assembly within balloon.

The present disclosure also provides a method treating an obstruction within vasculature of a subject, the method comprising positioning a catheter within vasculature of a subject, the catheter comprising a sheath having a guidewire lumen, an inflation lumen, a proximal end and a distal end, at least one electrode assembly adjacent to the guidewire lumen, wherein the at least one electrode assembly is coupled to the sheath and an electrical generator, wherein the electrical generator produces an electrical pulse, a balloon assembly circumferentially arranged around a portion of the sheath and around at least one electrode assembly, one or more liquid medium ports disposed within the sheath and within the balloon assembly, and positioning the balloon assembly adjacent an obstruction within the vasculature, inflating the balloon assembly by delivering a gas saturated liquid medium through the inflation lumen and out one or more liquid medium ports into the balloon assembly until a desired inflation pressure is obtained, and activating the at least one electrode assembly within the balloon to produce at least one pulse of electrical energy from the electrode assembly, whereupon the electrical energy reacts with the gas saturated liquid medium and generates one or more pressure waves that propagate through the balloon and disrupt at least a portion of the vascular obstruction.

A method according to the previous paragraph, wherein the gas-saturated liquid medium comprises a super saturated liquid medium.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "catheter" as used herein generally refers to a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "balloon catheter" as used herein generally refers to the various types of angioplasty catheters which carry a balloon for performing angioplasty. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

The term "electrically-induced pressure wave" as used herein is a pressure wave caused by a reaction between an electrical energy, such as an electrical and/or plasma arc, and a fluid. The electrically-induced pressure wave may be produced in air or liquid, such as saline that includes a contrast medium.

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "pressure wave" as used herein includes both a shock wave and a sound wave, wherein the shock wave is a pressure wave that moves above the velocity of sound, and the sound wave is a pressure wave that moves at or below the speed of sound.

The term "shock wave" as used herein shall mean a region of abrupt change of pressure moving as a wave front above the velocity of sound.

The term "sound wave" as used herein is pressure wave of audible or inaudible sound. That is, a sound wave is a pressure wave that moves at or below the speed of sound. An "acoustic wave" may also be referred to as a sound wave.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The terms "vasculature" and "vascular" as used herein refer to any part of the circulatory system of a subject, including peripheral and non-peripheral arteries and veins. Vascular material found within the vasculature can be comprised of both biological material (for example, nucleic acids, amino acids, carbohydrates, polysaccharides, lipids and the like) and non-biological material (for example, fat deposits, fibrous tissue, calcium deposits, remnants of dead cells, cellular debris and the like).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 6 is a representative cross-sectional view of a portion of a variation of an electrically-induced angioplasty balloon catheter of the present disclosure, wherein a balloon comprises an pressure-wave reflective material;

FIG. 12A is an elevation view of a kit that includes an electrode catheter radially disposed within a handle and a sheath and over a guidewire, according to one embodiment of the present disclosure;

FIG. 12B is a detail elevation view of the electrode catheter and the handle of FIG. 12A at a proximal end of the handle;

FIG. 13C is an elevation view of the handle of FIG. 12A, wherein several external components are partially transparent to illustrate internal components, and the shaft is shown in the proximal position;

FIG. 13D is an elevation view of the handle of FIG. 12A, wherein several external components are partially transparent to illustrate internal components, and the shaft is shown in an intermediate position;

FIG. 13E is an elevation view of the handle of FIG. 12A, wherein several external components are partially transparent to illustrate internal components, and the shaft is shown in a distal position;

FIG. 13F is a cross-sectional view of the handle of FIG. 12A, wherein the shaft is shown in the proximal position;

FIG. 13G is a cross-sectional view of the handle of FIG. 12A, wherein the shaft is shown in an intermediate position;

FIG. 13H is an exploded view of the handle of FIG. 12A;

FIG. 13J is another detail exploded view of the handle of FIG. 12A;

DETAILED DESCRIPTION

The present disclosure relates generally to the use of medical devices for the treatment of vascular conditions. In particular, the present disclosure provides materials and methods for using electrode-induced pressure waves to disrupt vascular blockages and to deliver therapeutic agents to the blockage area.

Figure 1A:
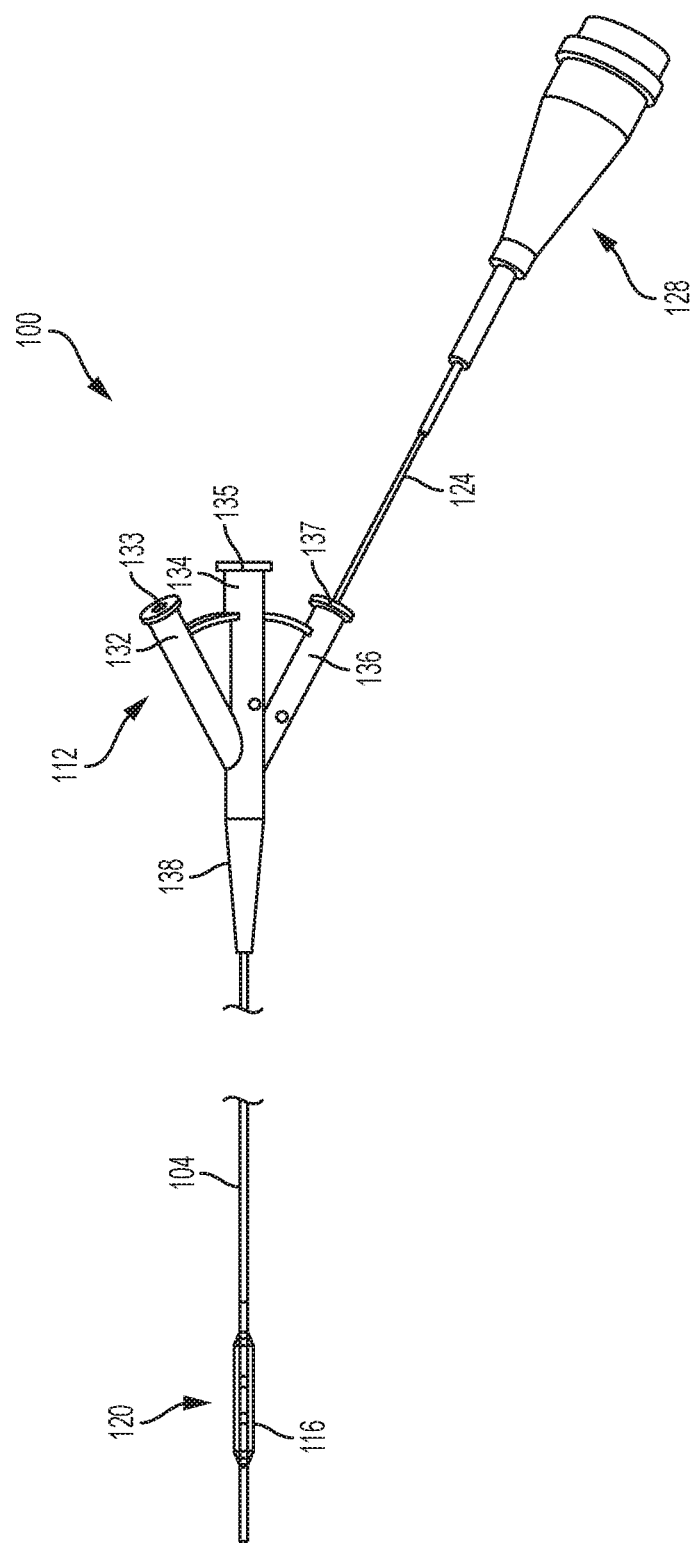
FIG. 1A is an elevation view of one variation of an electrically-induced angioplasty balloon catheter.
Figure 1B:
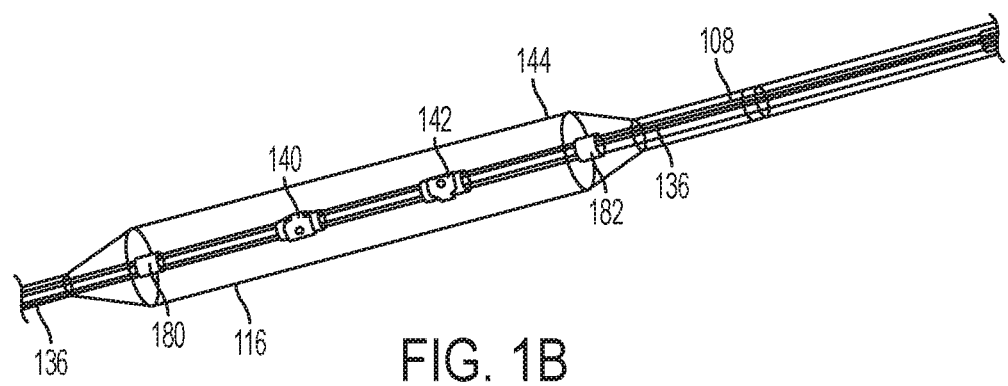
FIG. 1B is a perspective view of the distal portion of a variation of an electrically-induced angioplasty balloon catheter that includes multiple electrodes within a balloon.
Figure 1C:
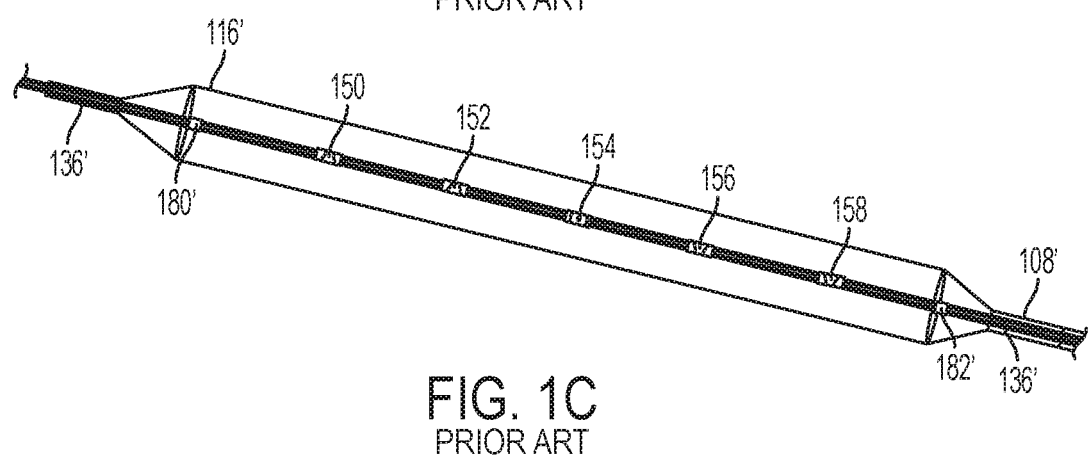
FIG. 1C is a perspective view of the distal portion of another variation of an electrically-induced angioplasty balloon catheter that includes multiple electrodes within a balloon.

Referring to FIG. 1A-1C, there is depicted an electrically-induced angioplasty balloon catheter system 100 comprising an electrode catheter included within a balloon to produce a pressure wave emanating from the balloon. The electrically-induced angioplasty balloon catheter system 100 may be used in angioplasty procedures in a patient's vascular system, such as in treatment of coronary arterial disease and peripheral arterial disease. The electrically-induced angioplasty balloon catheter system 100 may comprise a balloon catheter 104 and one or more stationary or slidable electrode assemblies 120 coupled to an electrode catheter 124. The balloon catheter 104 comprises a catheter 108, a proximal hub 112 coupled to the proximal end of the catheter 104, and the balloon 116 coupled to the distal end of the catheter 104. The electrode assemblies 120 may be a component of an electrode catheter 124, which may include the one or more electrode assemblies 120 at its distal end and a high-voltage connector 128 at its proximal end. Upon inserting the electrode catheter 124 into the balloon catheter 104, the electrode assemblies 120 will be disposed within the balloon 116.

The proximal hub 112 may be a bifurcate design or a trifurcate design. FIG. 1A illustrates the proximal hub 112 having a trifurcate design, which includes a central shaft 134, a first side shaft 132 and a second side shaft 136. The first and second side shafts are attached to either side of the central shaft 134. The central shaft 134 may have a proximal opening 135 that is connected to an inner lumen (not shown) of the proximal hub 112. The inner lumen extends through the length of the central shaft 134 and terminates at a distal opening (not shown) of the proximal hub 112. The proximal hub 112 may optionally comprises a strain relief portion 138, and if so, the inner lumen will pass through and exit the strain relief 138 member, thereby allowing the proximal hub 112 to be in fluid communication with the catheter 108.

The inner lumen may also be in communication and/or continuous with the guide wire lumen (not shown) of the catheter 138. The first side shaft 132 may have an opening 133 that is coupled to the inner lumen or a separate lumen within the proximal hub 112, and the second side shaft 136 may have an opening 137 that is coupled to the inner lumen or a separate lumen within the proximal hub 112. For example, the central shaft 134, the first side shaft 132 and the second side shaft 136 may all be coupled with and in fluid communication with the same inner lumen of the proximal hub 112, or the central shaft 134, the first side shaft 132 and the second side shaft 136 may be coupled with and in fluid communication with three separate lumens within the proximal hub 112. That is, the first side shaft 132 may serve as an inflation port for an inflation fluid, which may include saline and/or imaging contrast agent, for inflating the balloon 116. If so, the inflation fluid will travel through an inflation lumen in the proximal hub 112 and a corresponding inflation lumen within the catheter 108 which opens into the balloon 116. The central shaft 134 may serve as a guidewire port for guidewire to be inserted through the inner lumen of the proximal hub, and a corresponding guidewire lumen that travels through and beyond the catheter 104 and the balloon 116. The second side shaft 136 may serve as a port the electrode catheter 124. If so, the electrode catheter 124 will enter the opening 137 and travel through a separate lumen that corresponds with a separate lumen in the catheter 108 which opens into the balloon 116. The inner lumens may each have a wider proximal region and a narrower distal region, which may act as a stop for the devices inserted into the shafts. In some variations, the proximal hub 112 may be made of injection molded polycarbonate.

Figure 2:
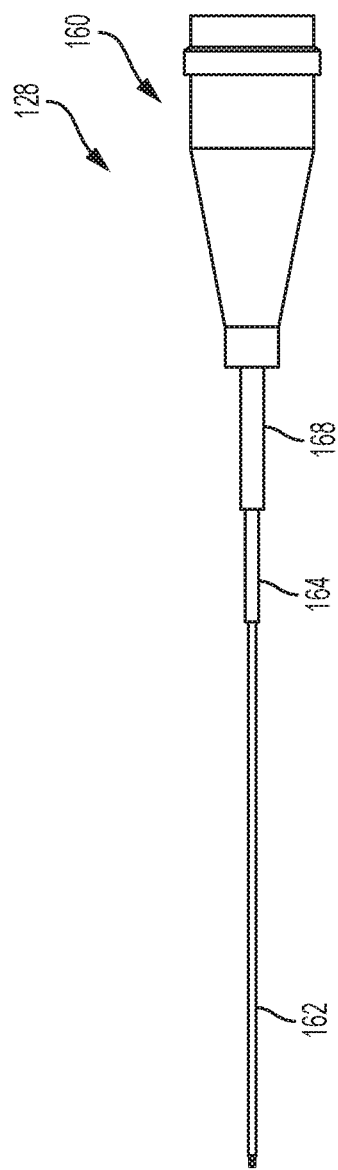
FIG. 2 is an elevation view of one variation of an electrode catheter that can be inserted into and slidable within an electrically-induced angioplasty balloon catheter.

Referring to FIG. 2, the high-voltage connector 128, which may be inserted through at least one of the central shaft 134, the first side shaft 132 and the second side shaft 136 of the proximal hub 112, may be configured to connect the electrode assemblies 120 to a high voltage pulse generator (not shown). The high voltage connector 128 may also include a cable 162 that may be enclosed in a jacket. The high voltage connector 128 may also include a first shaft region 168 and a second shaft region 164 that is narrower than the first shaft region 168, which may connect to cable 162. The first shaft region 168 may have a diameter that is greater than the diameter of the narrower portion of an inner lumen 133, 135, 137 of the proximal hub 112, but smaller than the diameter of the wider portion of the inner lumen. The second shaft region 164 distal to the first shaft region 168 may be configured for strain relief.

The cable 162 may comprise one or more wires that are coupled to corresponding electrode assemblies 120. The proximal end of the cable 162 extends to and connects with the high voltage connector 160, and the distal end of the cable 162 extends to and connects with the electrode assemblies 120. For example, the cable 162 may provide connections for both the high voltage pulse(s) and the return path between the voltage pulse generator and the electrode assemblies 120. In some variations, the cable 162 may provide one or more high voltage supply connections to the electrode assemblies 120, with one or more return connections. For example, the cable may provide for a single high voltage supply connection and a single return connection to the electrode assemblies. Alternatively, the cable 162 may provide for a plurality of high voltage supply connections (for example, four) and one or more return connections to the electrode assemblies 120.

The high voltage connector 160 electrically connects and couples to a high voltage pulse generator, thereby providing to the electrode assemblies 120 at the distal end of the catheter, particularly within the balloon. Pins within the high-voltage connector 160 may connect each of the wires from the electrode assemblies to the appropriate channel on a high voltage pulse generator. The cable 162 may be bonded to the high-voltage connector 160 and/or the proximal hub 112. As discussed above, the cable 162 may extend from a lumen of the proximal hub 112 and connect to the high-voltage connector 160. Pins within the high-voltage connector 160 may connect each of the wires from the electrode assemblies 120 to the appropriate channel on a high voltage pulse generator.

There may be any number of electrode assemblies 120 located at the distal end of the catheter and enclosed by the balloon 116. For example, there may be one electrode assembly, two electrode assemblies, four electrode assemblies, five electrode assemblies or more. FIGS. 1B and 1C depict the distal portions of electrically-induced angioplasty balloon catheter system 100 with two electrode assemblies and five electrode assemblies. FIG. 1B depicts one variation of an electrically-induced angioplasty balloon catheter system 100 comprising an elongate member 136, a first electrode assembly 140 at a first location along the length of the elongate member 136, a second electrode assembly 142 at a second location along the length of the elongate member 136, and a balloon 116 configured to be filled with a fluid to sealably enclose the first electrode assembly 140 and second electrode assembly 142. The balloon 116 may be made of an electrically insulating material that may be rigid (for example, PET, etc.), semi-rigid (for example, PBAX, nylon, PEBA, polyethylene, etc.), or flexible (for example, polyurethane, silicone, etc.). The first and second electrode assemblies may be spaced apart along the length of the elongate member, and may be from about 3 mm to about 20 mm apart from each other, for example, about 5 mm, 7 mm, 10 mm. The length of the balloon may vary depending on the number of electrode assemblies and the spacing between each of the electrode assemblies. For example, a balloon 116 for an electrically-induced angioplasty balloon catheter system 100 with two electrode assemblies spaced about 7 mm apart (for example, 6.7 mm) may have a length of about 20 mm. A balloon for an electrically-induced angioplasty balloon catheter system 100 with five electrode assemblies spaced about 10 mm apart may have a length of about 60 mm. The electrode assemblies 140, 142 each comprise two inner electrodes that are positioned circumferentially opposite each other, an insulating sheath with two openings aligned over the two inner electrodes, and an outer electrode sheath with two openings that are coaxially aligned with the two openings of the insulating sheath.

Each of the electrode assemblies 140, 142 are configured to generate a pair of directed sparks or electrical arcs. Upon creating the electrical arc in the liquid medium and the liquid medium absorbing the electrical energy, a pressure wave is created in the liquid medium and cavitation bubbles are produced. There exists a potential discrepancy in the field as to whether the cavitation bubble is produced prior to, simultaneously with, or after the generation of the pressure waves. Nevertheless, the pressure waves penetrate and/or pass through the balloon assembly 140, and the formation of the cavitation bubbles expands the diameter of the balloon assembly. The electrode assemblies 504, 506 may generate pressure waves that propagate outward from different locations around the circumference of elongate member 136. For example, the electrode assembly 140 may generate pressure waves that propagate from the left and right longitudinal side of the elongate member, while the electrode assembly 142 may generate pressure waves that propagate from the top and bottom longitudinal side of the elongate member. In some variations, the electrode assembly 140 may generate a pair of pressure waves that propagate outward from positions at 0 degrees and 180 degrees around the circumference of the elongate member 142, while the electrode assembly 506 may generate a pair of pressure waves that propagate outward from positions at 60 degrees and 240 degrees around the circumference of the elongate member. In still other variations, electrode assemblies 140, 142 may each generate a pair of pressure waves that propagate outward at the same locations around the circumference of the elongate member, but from different locations along the length of the elongate member. Optionally, a radiopaque marker bands may be provided along the length of the elongate member to allow a practitioner to identify the location and/or orientation of the electrode catheter as it is inserted through balloon catheter and/or the vasculature of a patient. For example, there may be a first marker band proximal to the first electrode assembly and a second marker band distal to the second electrode assembly. In some variations, one or more marker bands may be located proximal to the proximal-most electrode assembly, and/or distal to the distal-most electrode assembly, and/or in the center of the elongate member and/or any other location along the length of the elongate member.

FIG. 1C depicts another electrically-induced angioplasty balloon catheter system 100' comprising an elongate member 136', a first electrode assembly 150, a second electrode assembly 152, a third electrode assembly 154, a fourth electrode assembly 156, a fifth electrode assembly 158, and a balloon 116' configured to be filled with a fluid to sealably enclose the first, second, third, fourth, and fifth electrode assemblies. The balloon 116' may be made of an electrically insulating material that may be rigid (for example, PET, etc.), semi-rigid (for example, PBAX, nylon, PEBA, polyethylene, etc.), or flexible (for example, polyurethane, silicone, etc.). The electrode assemblies of the electrically-induced angioplasty balloon catheter system 100' may be similar to the ones described in FIG. 1B, and/or may be similar to any of the electrodes described herein. The elongate member 136' may be a catheter with a longitudinal guide wire lumen. Each of the electrode assemblies are configured to generate a pair of pressure waves that propagate in two opposite directions from the side of the elongate member. The electrode assemblies of FIG. 1C may be configured to generate pressure waves that propagate outward from different locations around the circumference of elongate member, as described above for FIG. 1B. Although the figures herein may depict pressure wave devices with two or five electrode assemblies, it should be understood that a pressure wave device may have any number of electrode assemblies, for example, 3, 4, 6, 7, 8, 9, 10, 15, 20, etc. The electrode assemblies may be spaced apart along the length of the elongate member, and may be from about 3 mm to about 10 mm apart from each other, for example, about 5 mm, 8 mm, 10 mm, etc. depending on the number of electrode assemblies and the length of the elongate member that is enclosed within the balloon. Electrically-induced angioplasty balloon catheter system 100 with one or more electrode assemblies distributed along the length of a catheter may be suitable for use in angioplasty procedures to break up calcified plaques that may be located along a length of a vessel. Each electrode assembly may have a first electrode, a second electrode, and an insulating layer between the first electrode and second electrode. The electrodes may be made of materials that can withstand high voltage levels and intense mechanical forces (for example, about 1000-2000 psi or 20-200 ATM in a few microseconds) that are generated during use. For example, the electrodes may be made of stainless steel, tungsten, nickel, iron, steel, and the like. The insulating layer 2 may be made of any material with a high breakdown voltage, such as Kapton, ceramic, polyimide or Teflon. A more detailed description of the electrode assemblies is included in U.S. Pat. No. 8,747,416 which is hereby incorporated herein by reference in its entirety for all that it teaches and for all purposes.

Figure 3:
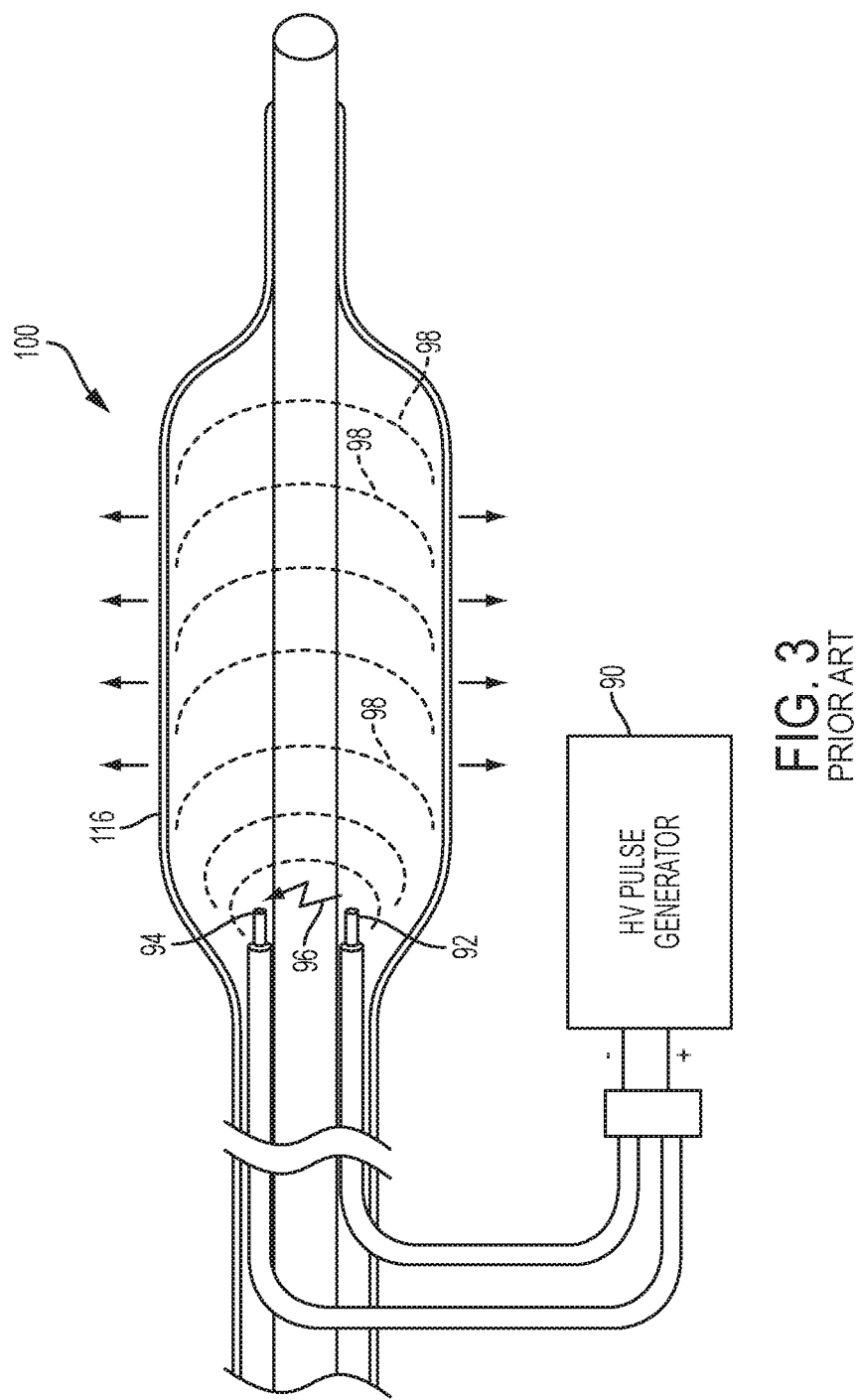
FIG. 3 is an elevation view and/or schematic of an electrically-induced angioplasty balloon catheter depicting an arc between the electrodes and simulations of the pressure wave flow emanating from the reaction between the electrical arc and the fluid within the balloon.

Each electrode assembly may be attached to a source of high voltage pulses, ranging from 100 to 10,000 volts for various pulse durations. A schematic of the electrode assemblies is included in U.S. Pat. No. 9,072,534 which is hereby incorporated herein by reference in its entirety for all that it teaches and for all purposes. For example, referring to FIG. 3, there is depicted a view of the catheter illustrating a high voltage pulse generator 190 coupled to positive electrode 94 and negative electrode 92. Upon the high voltage pulse generator 190 delivering a stream of electrical pulses to the positive and negative electrodes 94, 92, are an arc 96 between the electrodes 92, 94 within an electrode assembly is created within the fluid filled balloon, thereby creating pressure wave flow 98. The high voltage pulse generator 190 includes controls to allow an operator to adjust the magnitude of the pulsed voltage, the current, the duration and repetition rate, thereby controlling the magnitude of the pressure wave.

Figure 4:
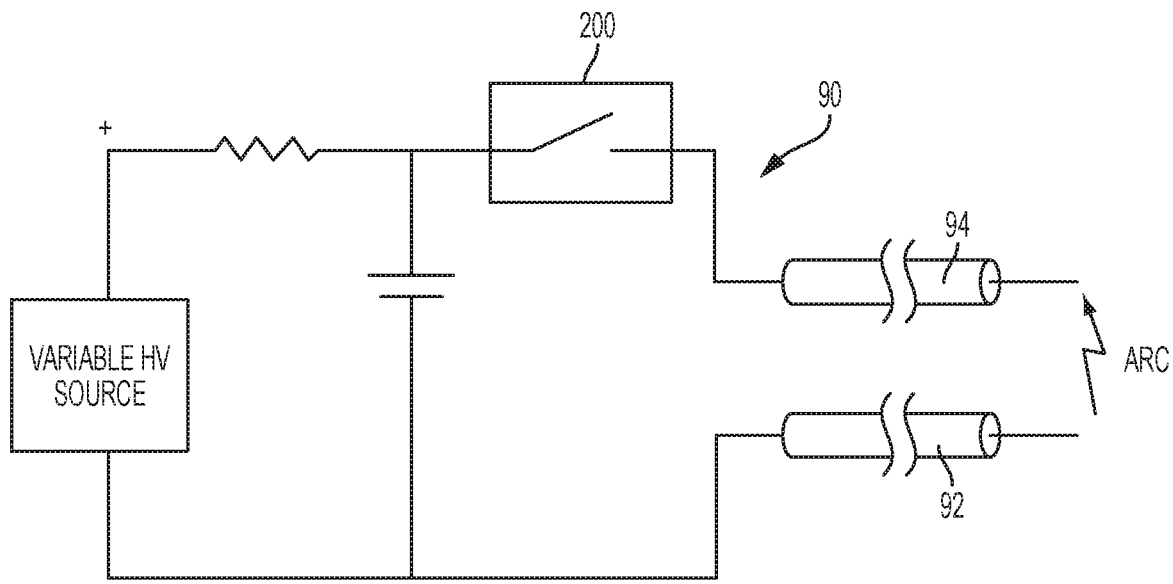
FIG. 4 is a schematic of a high voltage pulse generator connected to the electrodes, which create the arc.
Figure 4A:
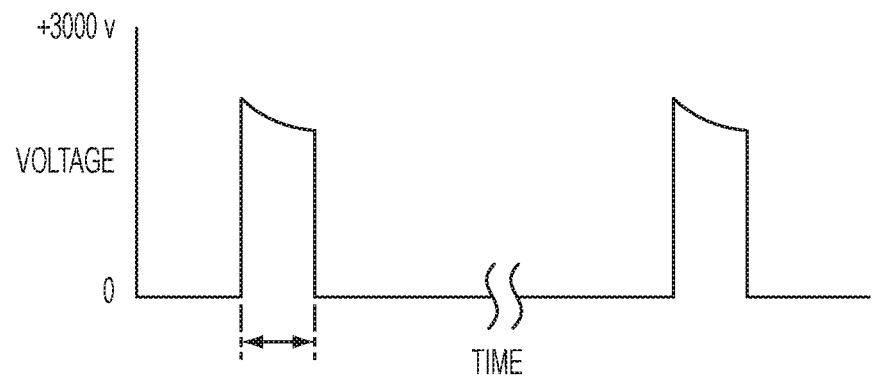
FIG. 4A depicts voltage pulses that may be produced by the high voltage pulse generator of FIG. 4.

Referring to FIG. 4, there is depicted a schematic of the high voltage pulse generator 90. And FIG. 4 shows a resulting waveform. The voltage needed will depend on the gap between the electrodes and is generally 100 to 3000 volts. A high voltage switch 91 can be set to control the duration of the pulse. The pulse duration will depend on the surface area of the positive and negative electrodes 92, 94 and needs to be sufficient to generate a gas bubble at the surface of the electrode causing a plasma arc of electric current to jump the bubble and create a rapidly expanding and collapsing bubble, which creates the mechanical pressure wave in the balloon. Such pressure waves can be as short as a few microseconds. Since both the rapid expansion and the collapse create pressure waves, the pulse duration can be adjusted to favor one over the other. A large steam bubble will generate a stronger pressure wave than a small one. However, more power is needed in the system to generate this large steam bubble. Traditional lithotripters try to generate a large steam bubble to maximize the collapsing bubble's pressure wave. By adjusting the pulse width to a narrow pulse less than two microseconds or even less than one microsecond a rapidly expanding steam bubble and pressure wave can be generated while at the same time the final size of the steam bubble can be minimized. The short pulse width also reduces the amount of heat in the balloon to improve tissue safety.

FIG. 4 only depicts one electrode assembly comprising positive and negative electrodes 94, 92, and FIG. 4 only depicts one variable high voltage source coupled to the electrode assembly. But it shall be understood that multiple electrode assemblies may be coupled to the high voltage pulse generator 90. In the event that multiple electrode assemblies are coupled to the same high voltage pulse generator 90, the electrode assemblies and the high voltage pulse generator 90 may be configured such that the high voltage pulse generator 90 provides power to the electrode assemblies so that the electrode assemblies produce and/or emits electrical pulses simultaneously, serially or according to another firing sequence. Additionally, it shall also be understood that each multiple electrode assembly may be coupled to an independent high voltage pulse generator 90 such that each electrode assembly is independently controlled, and each electrode assembly produces and/or emits separate electrical pulses. A more detailed description of how the high voltage pulse generator and/or the electrode assemblies are controlled is included in U.S. Pat. Nos. 8,728,091 and 8,747,416 and 9,011,463 and 9,138,249 which are hereby incorporated herein by reference in its entirety for all that they teach and for all purposes.

Figure 5:
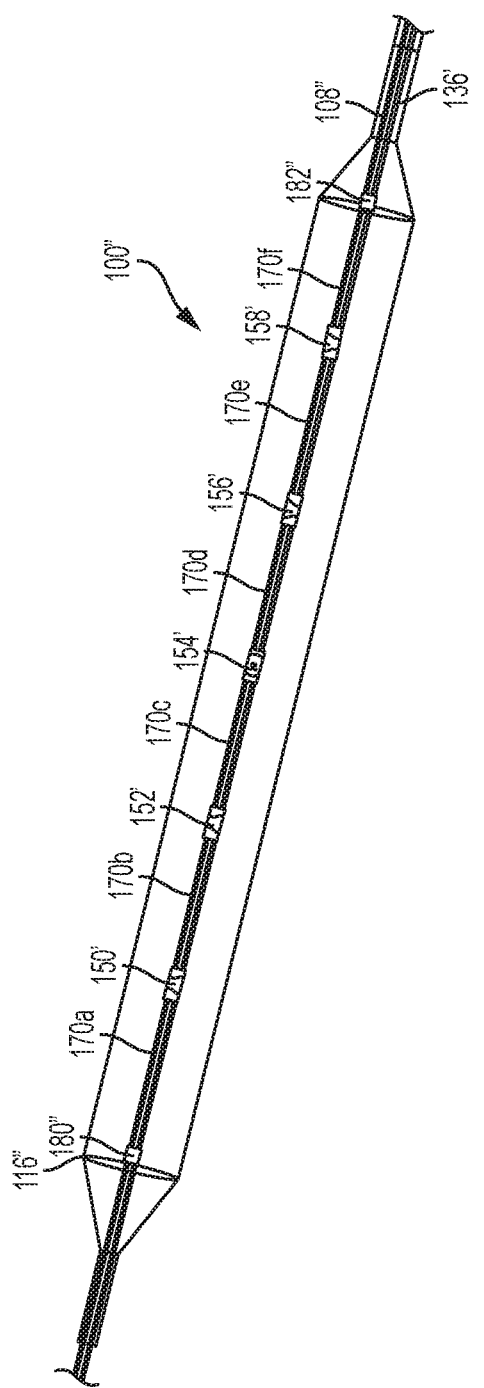
FIG. 5 is a perspective view of the distal portion of another variation of an electrically-induced angioplasty balloon catheter that includes multiple electrodes within a balloon.

Referring to FIG. 5, there is depicted an alternate version of the balloon-catheter system 100". As shown in FIG. 5, the electrically-induced angioplasty balloon catheter system 100" includes an elongated member 136" and a series of electrode assemblies separated by a series of tubular sleeves. This version of the electrically-induced angioplasty balloon catheter system 100" is a low-profile design because the diameters of the electrode assemblies and the tubular sleeves are relatively consistent, thereby having a relatively constant, low profile. Continuing to refer to FIG. 5, a first electrode assembly 150', a second electrode assembly 152', a third electrode assembly 154', a fourth electrode assembly 156', and a fifth electrode assembly 158', are separated by a series of tubular sleeves 170$b$, 170$c$, 170$d$ and 170$e$. The electrically-induced angioplasty balloon catheter system 100" may also include two radiopaque markers 180" and 182" which are axially aligned with the working ends of the balloon 116". If so, one or more of the tubular sleeves 170$a$, 170$f$ may be placed between a radiopaque marker 180', 182' and an adjacent or neighboring electrode assembly neighboring electrode assembly 150', 158'. The device may include any suitable number of electrode assemblies, marker bands, and tubular sleeves. All electrode assemblies, marker bands, and tubular sleeves are enclosed by balloon 116". In some variations, the tubular sleeve having an end that is adjacent to either electrode assemblies or the radiopaque markers may be tapered or flared to accommodate an electrode assembly's or the radiopaque marker's outer diameter that is smaller or larger, respectively, than the outer diameter of a neighboring electrode assembly or the radiopaque marker. For example, if a tubular sleeve has a tapering outer profile, one sleeve end may overlap an inner electrode sheath of an electrode assembly, and the other sleeve end may overlap the radiopaque marker. Similarly, if a tubular sleeve has a tapering outer profile, one sleeve end may overlap an inner electrode sheath of an electrode assembly, and the other sleeve end may overlap an inner electrode sheath of another electrode assembly. The radiopaque marker's outer diameter may be less than the diameter of an outer electrode sheath, and a tubular sleeve may have an outer profile that tapers from the electrode assembly to the radiopaque marker. In other variations, the tubular sleeve maintains a consistent diameter throughout its length regardless of whether it is placed between two electrode assemblies or between an electrode assembly and a marker band. A more detailed description of the low-profile version is included in U.S. Publication No. 2015-0039002 A1 which is hereby incorporated herein by reference in its entirety for all that it teaches and for all purposes.

Figure 5A:
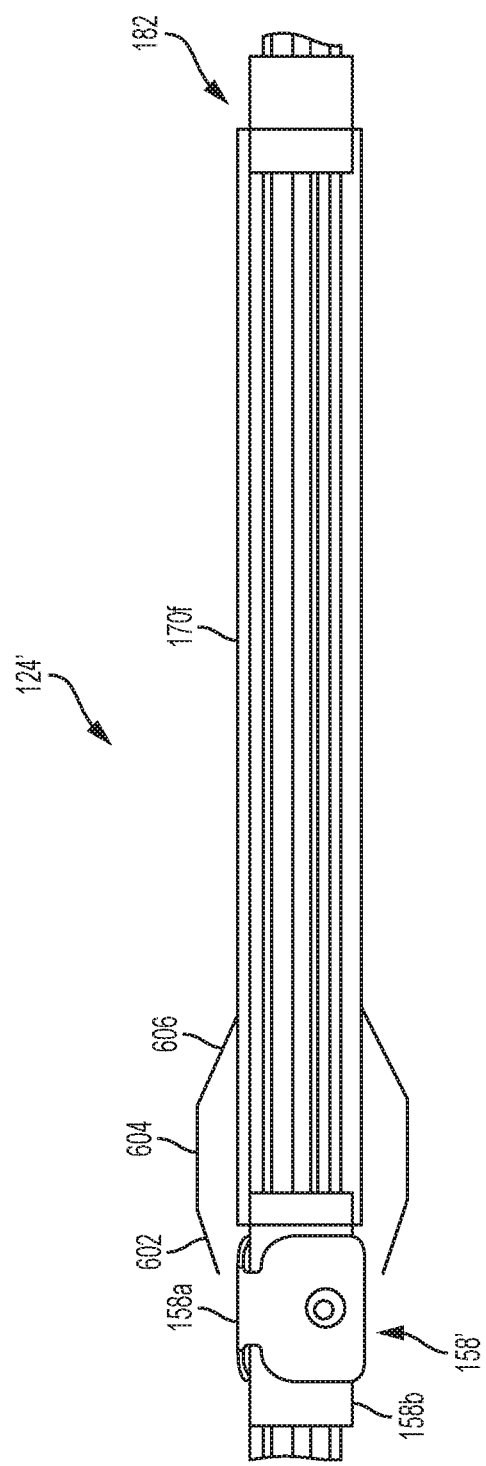
FIG. 5A is an elevation view of an enlarged portion of the electrode catheter included within the electrically-induced angioplasty balloon catheter of FIG. 5.

Referring to FIG. 5A, there is depicted a portion of the electrode catheter 124' illustrated in FIG. 5. Specifically, the portion illustrated in FIG. 5A includes the portion of the electrode catheter 124' between the electrode assembly 158' and the radiopaque marker 182". As shown in FIG. 5A, the electrode assembly 158' includes an insulating sheath 158$b$ and an outer electrode sheath 158$a$. The electrode catheter 124' also includes a tubular sleeve 170*f* axially disposed between the electrode assembly 158' and the radiopaque marker 182'. The diameter of the electrode assembly 158' is substantially the same or equal to the diameter of the tubular sleeve 170*f*. The electrode catheter 124' also includes a shield or deflector 604 that is capable of deflecting the pressure wave(s) toward the guidewire and/or guidewire lumen of the electrode catheter 124' in order to vibrate the guidewire passing therethrough.

It may also be desirable to excite and vibrate the guidewire to increase the guidewire's ability to pierce and cross the occlusion. Accordingly, the present disclosure also contemplates directing the pressure waves caused by creating an electrical spark across the electrodes in the liquid medium to propagate pressure waves toward the guidewire lumen and/or guidewire such that the pressure waves excite and vibrate the guidewire. One end 606 of the deflector 604 depicted in FIG. 5A is coupled to the tubular sheath 170*f*, and the other end of the deflector 602 is disposed such that it is radially offset but axially aligned with at least a portion of the electrode assembly 158'. Upon creation of the pressure wave, the deflector deflects the pressure wave(s) toward the guidewire and/or guidewire lumen of the electrode catheter 124' in order to vibrate the guidewire passing therethrough. For example, the distal portion 602 of the deflector 604 is tapered such that the pressure wave will reflect off the deflector 604 and move radially inward away from the electrode assembly 158'. Although FIG. 5A depicts only a portion of the deflector 604 being axially aligned with a portion of the electrode assembly 158', the present disclosure contemplates disposing the deflector 604 in a position with respect to the electrode assembly 158' such that it is axially aligned with the entire electrode assembly 158'. Additionally, although FIG. 5A depicts the deflector 604 being coupled to one tubular sheath 170*f*, the deflector may be coupled to another tubular sheath, namely the tubular sheath 170*e*, and/or the deflector may be coupled to both tubular sheaths 170*e*, 170*f* such that the deflector spans axially over the electrode assembly 158'.

Referring to FIG. 6, there is depicted another alternate embodiment of the balloon catheter 600 of the present disclosure, particularly an alternate embodiment of the balloon catheter that comprises a pressure-wave reflective element 680 over the balloon 616. The pressure-wave reflective element 680 may also be referred to as a porous attenuating member. The pressure-wave reflective element 680 has multiple purposes, namely (1) the pressure-wave reflective element 680 reduces or prevents the formation of cavitation bubbles exterior of the pressure-wave reflective element 680 and/or the balloon 616, (2) upon the pressure waves reaching the pressure-wave reflective element 680, the reflective element 680 re-directs at least a portion of the pressure waves toward the guidewire lumen 610 of catheter sheath 608 and/or guidewire (not shown) to excite and/or vibrate the guidewire, and (3) the pressure-wave reflective element 680 reinforces the balloon 616, Accordingly, the pressure-wave reflective element 680 is (1) a means for reducing or preventing the formation of cavitation bubbles exterior of the pressure-wave reflective element 680 and/or the balloon 616, (2) a means for re-directing at least a portion of the pressure waves toward the guidewire lumen 610 and/or guidewire to excite and/or vibrate the guidewire, and/or (3) a means for reinforcing the balloon 616.

Although the pressure-wave reflective element 680 is illustrated over the balloon 616 in FIG. 6, the pressure-wave reflective element 680 may be on the inside (interior) of the balloon 616, such as an inside layer, or the pressure-wave reflective element 680 may be incorporated or integrated into the balloon 616 itself. Additionally, the pressure-wave reflective element 680 may cover a portion of the balloon 616, as depicted in FIG. 6, or the pressure-wave reflective element 680 may cover the entire balloon 616. Regardless of whether the pressure-wave reflective element 680 is directly or indirectly coupled to the balloon 616, the pressure-wave reflective element 680 is capable of expanding and contracting with the balloon 616. Accordingly, both the pressure-wave reflective element 680 and the balloon 616 have an expanded state and a contracted state.

The pressure-wave reflective material may include a polymer having a higher or harder durometer in comparison to the materials traditionally used in balloons, such as polyethylene, polyurethane, and polytetrafluoroethylene. The increased durometer and hardness of the pressure-wave reflective material may be achieved by including a filler within the polymer matrix of a single layered balloon, increasing the cross-linking between polymer within the single layered balloon, selecting a harder polymer (in comparison to the traditional balloon materials), or co-extruding an additional harder polymer layer with the traditional polymer layer. If a co-extruded construction is used to manufacture the balloon, then the harder layer may be included on either the interior or exterior of the balloon, and the traditional layer having the lower hardness will be on the opposite side of the balloon. Additionally, a three layered co-extruded structure may be used to manufacture the balloon such that the harder layer is sandwiched between two traditional lower durometer layers.

The pressure-wave reflective element 680 may be directly coupled to the working portion 670 of the balloon 616 or indirectly coupled to the working portion 670 of the balloon 616. The pressure-wave reflective element 680 may be directly coupled to the working portion 670 of the balloon 616 by being affixed to the working portion 670 by a chemical bond, mechanical fixation or some other means of affixation. The pressure-wave reflective element 680 may be indirectly coupled to the working portion 670 of the balloon 616 by directly coupling the pressure-wave reflective element 680 to the proximal end of the balloon 616, the distal end of the balloon 616, the tapered ends of the balloon, and/or the catheter sheath 608, including the structure that creates the guidewire lumen. Indirectly coupling the pressure-wave reflective element 680 to the working portion 670 of the balloon 616 allows the pressure-wave reflective element 680 to expand and contract with the balloon 616 upon inflation and deflation, respectively, but it also allows the pressure-wave reflective element 680 to expand and contract in a manner such that the pressure-wave reflective element 680 is not permanently attached to the working portion 670 of the balloon 616. That is, indirectly coupling the pressure-wave reflective element 680 to the working portion 670 of the balloon 616 allows the pressure-wave reflective element 680 to expand and contract separately from the balloon 616 but respectively with the balloon.

The pressure-wave reflective element 680 may be constructed of a biocompatible material, including either a polymeric material or a metallic material, such as nitinol, which is also known as nickel titanium. The pressure-wave reflective element 680 may be a solid structure or a porous scaffolding structure, as shown in FIG. 6. As discussed in more detail below, the present disclosure contemplates that the pressure-wave reflective element 680 may comprise various shapes and configuration. For example, the sizes of the pores or openings within the scaffolding structure may be adjusted to control the amount of pressure waves that are reflected toward the guidewire lumen 610 and/or guidewire.

Regarding the pressure-wave reflective element's ability to reduce or prevent the formation of cavitation bubbles exterior of the pressure-wave reflective element 680 and/or the balloon 616, it may be preferable for the pressure-wave reflective element 680 to be porous and thereby have openings. Referring to FIGS. 6A-6F, the openings 685 within the pressure-wave reflective element 680 may prevent the formation of large sized cavitation bubbles on the exterior of the balloon 616. The openings 685 not only allow the pressure waves to pass therethrough, but the quantity and size of the openings 685', particularly with respect to the remainder of the structural mass 687 (or portions thereof) of pressure-wave reflective element 680, may also limit the size of the cavitation bubbles that can form on the exterior of the balloon 616. The relationship between the open area and the closed area (or the ratio of the open area to the overall area) within the pressure-wave reflective element 680 should be such that a sufficient amount of the pressure waves pass through the pressure-wave reflective element 680. And the size of the openings 885 should allow the pressure waves to pass therethrough, while also limiting the size of the cavitation bubbles that can form on the exterior of the balloon 616. Accordingly, it may be desirable for the percentage of the open area to the overall area of the pressure-wave reflective element 680 to be between 1 percent-99 percent, including any increment therebetween such as 2 percent, 3 percent, 4 percent, 5 percent, 6 percent, 7 percent, 8 percent, 9 percent, 10 percent, . . . , 15 percent . . . 20 percent, . . . , 25 percent, . . . , 30 percent, . . . 35 percent, . . . , 40 percent, . . . , 45 percent, . . . , 50 percent, . . . , 55 percent, . . . , 60 percent, . . . 65 percent, . . . , 70 percent, . . . , 75 percent, . . . , 80 percent, . . . , 85 percent, . . . , 90 percent, 91 percent, 92 percent, 93 percent, 94 percent, 95 percent, 96 percent, 97 percent, and 98 percent. It may also be desirable for the ratio of the open area to the overall area of the pressure-wave reflective element 680 to be within a particular range such as between 5 percent to 95 percent, 10 percent to 90 percent, 15 percent to 85 percent, 20 percent to 80 percent, 25 percent to 75 percent, 30 percent to 70 percent, 35 percent to 65 percent, 40 percent to 60 percent, and 45 percent to 55 percent. Additionally, for any of the above listed ratios it may be desirable for each opening 685 to have a particular size, such as between 50 microns to 1000 microns (1 millimeter), including any increment therebetween such as 100 microns, . . . , 125 microns, . . . , 150 microns, 175 microns, . . . , 200 microns, . . . , 225 microns, . . . , 250 microns, . . . , 300 microns, . . . , 325 microns, . . . , 350 microns, . . . , 400 microns, . . . , 425 microns, . . . , 450 microns, . . . , 475 microns, . . . , 500 microns, . . . , 525 microns, . . . , 550 microns, . . . , 575 microns, . . . , 600 microns, . . . , 625 microns, . . . , 650 microns, . . . , 675 microns, . . . , 700 microns, . . . , 725 microns, . . . , 750 microns, . . . , 775 microns, . . . , 800 microns, . . . , 825 microns, . . . , 850 microns, . . . , 875 microns, . . . and 950 microns. It may also be desirable for the size openings 685 within the pressure-wave reflective element 680 to be within a particular range such as between 100 to 900 microns, 150 to 850 microns, 200 to 800 microns, 250 to 750 microns, 300 to 700 microns, 350 to 650 microns, 400 to 600 microns, and 450 to 550 microns.

Figure 6A:
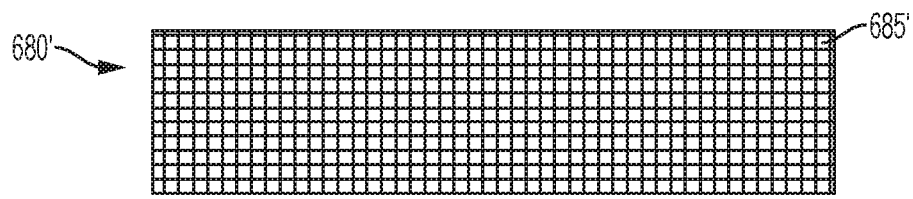
FIG. 6A is a side elevation view of a pressure-wave reflective element comprising a plurality of square-shaped openings, according to one variation of the present disclosure.
Figure 6B:
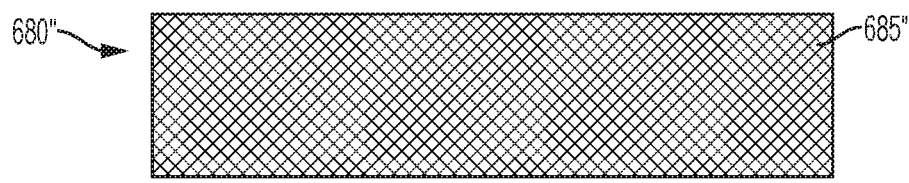
FIG. 6B is a side elevation view of a pressure-wave reflective element comprising a plurality of diamond-shaped openings, according to an alternative variation of the present disclosure.
Figure 6C:
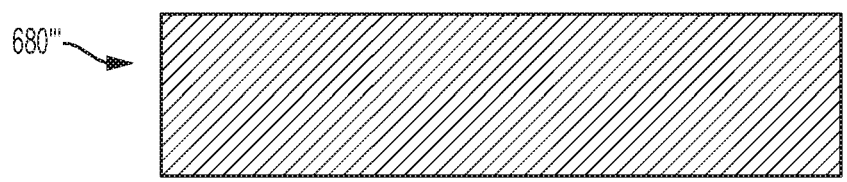
FIG. 6C is a side elevation view of a pressure-wave reflective element comprising a plurality of openings formed by a helical structure wound in a particular direction, according to another alternative variation of the present disclosure.
Figure 6D:
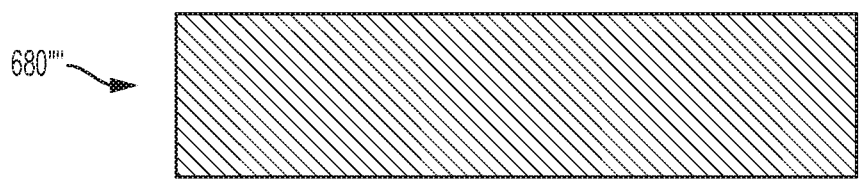
FIG. 6D is a side elevation view of a pressure-wave reflective element comprising a plurality of openings formed by a helical structure wound in a particular direction, according to another alternative variation of the present disclosure.
Figure 6E:
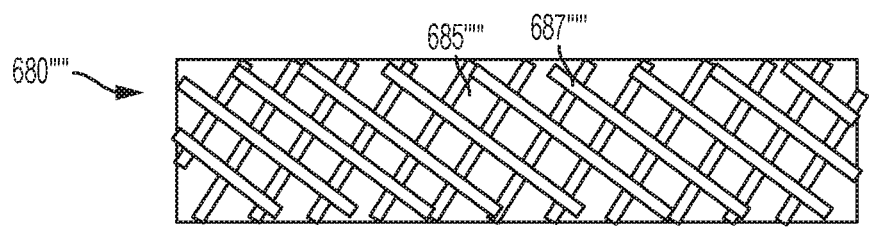
FIG. 6E is a side elevation view of a pressure-wave reflective element comprising a plurality of openings formed by a helical wound ribbons, according to another alternative variation of the present disclosure.
Figure 6F:
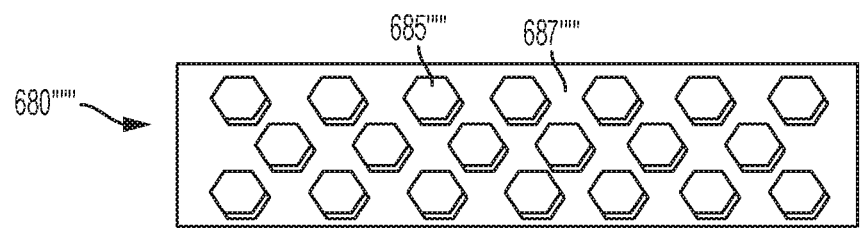
FIG. 6F is a side elevation view of a pressure-wave reflective element comprising a plurality of hexagon-shaped openings, according to another alternative variation of the present disclosure.

The openings 685' in the pressure-wave reflective element 880' depicted in FIG. 6A are shown as squares, the openings 685" (and 685"") in the pressure-wave reflective element 680" (and pressure-wave reflective element 680'") depicted in FIG. 6B (and FIG. 6E) are shown as diamonds, the openings 685"" the pressure-wave reflective element 680"" are shown as hexagons, which are disposed around the circumference of pressure-wave reflective element, as well as along its length. Although the openings of in the attenuating member in these figures are illustrated as squares, diamonds and hexagons, the openings may have an alternate shape, such as a circle, oval, triangle, rectangle, polygon, pentagon, heptagon, octagon, nonagon, and decagon. For example, FIG. 6C is a side view of a pressure-wave reflective element 680" comprising a plurality of openings formed by a helical structure wound in a particular direction (for example, clockwise or left to right), and FIG. 6D is a side view of a pressure-wave reflective element 616'" comprising a plurality of openings formed by a helical structure wound in an alternate direction (for example, counterclockwise or right to left). Additionally, the two helically formed pressure-wave reflective elements may be combined to form the pressure-wave reflective element 680"" depicted in FIG. 6E. The pressure-wave reflective element 680"" depicted in FIG. 6E is similar to the pressure-wave reflective element 680" depicted in FIG. 6B, but the porous attenuating member 680" depicted in FIG. 6B is braided and the pressure-wave reflective element 680"" depicted in FIG. 6E is wound or formed by one or two hypotubes. Additionally, the structural mass 687"" (or portions thereof) of the pressure-wave reflective element 780"" depicted in FIG. 6E is larger than the structural mass (or portions thereof) of the porous attenuating member 680" depicted in FIG. 6B because braided materials are generally smaller in size. Referring to FIG. 6F, the structural mass 687"" (or portions thereof) of the pressure-wave reflective element 780"", are substantial in comparison to the size of the hexagonal openings 685"". It may be desirable for the ratio of the area of the openings 685 to the area of the structural mass 687 of the pressure-wave reflective element 880 to be between 1:0.01 and 1:100, including any increment therebetween such as 1:0.01, 1:0.02, 1:0.03, 1:0.04, 1:0.05, 1:0.06, 1:0.06, 1:0.07, 1:0.08, 1:0.09, 1:0.10, . . . , 1:0.20, . . . , 1:0.30, . . . , 1:0.40, . . . , 1:0.50, . . . , 1:0.60, . . . , 1:0.70, . . . , 1:0.80, . . . , 1:0.90, 1:0.91, 1:0.92, 1:0.93, 1:0.94, 1:0.95, 1:0.96, 1:0.97, 1:0.98, 1:0.99, 1:1, 1:2, 1:3, 1:4, 1:5, 1:6, 1:7, 1:8, 1:9, 1:10, . . . , 1:15, . . . 1:20, . . . , 1:25, . . . , 1:30, . . . , 1:35, . . . , 1:40, . . . , 1:45, . . . , 1:50, . . . , 1:55, . . . , 1:60, . . . , 1:65, . . . , 1:70, . . . , 1:75, . . . , 1:80, . . . , 1:85, . . . , 1:90, 1:91, 1:92, 1:93, 1:94, 1:95, 1:96, 1:97, 1:98, 1:99, and 1:100. It may also be the ratio of the area of the openings 685 to the area of the structural mass 687 of the pressure-wave reflective element 680 to be within a particular range such as between 1:0.01 and 1:100, 1:0.10 and 1:90, 1:0.20 and 1:80, 1:0.30 and 1:70, 1:0.40 and 1:60, 1:0.50 and 1:50, 1:0.60 and 1:40, 1:0.70 and 1:30; 1:0.80 and 1:20, 1:0.90 and 1:10, 1:0.90 and 1:9, 1:0.90 and 1:8, 1:0.90 and 1:7, 1:0.90 and 1:6, 1:0.90 and 1:5, 1:0.90 and 1:4, 1:0.90 and 1:3, 1:0.90 and 1:2, or any increments therebetween, such as 1:0.91 and 1:1.9, 1:0.92 and 1:1.8, 1:0.93 and 1:1.7, 1:0.94 and 1:1.6, 1:0.95 and 1:1.5, 1:0.96 and 1:1.4, 1:0.97 and 1:1.3, 1:0.98 and 1:1.2 and 1:0.99 and 1:1.01.

The pressure-wave reflective element's ability to reduce or prevent the formation of cavitation bubbles exterior of the pressure-wave reflective element 680 and/or the balloon 616 potentially reduces the existence and/or the size of the cavitation bubbles formed on the exterior of the balloon assembly, which in turn reduces the likelihood that cavitation bubbles will be created and expand and contract between the balloon assembly and the vasculature wall. And reducing or preventing expansion and contraction of cavitation bubbles between the balloon assembly and the vasculature wall prevent or reduce the likelihood that a hydraulic force or pressure will be applied to the vascular occlusion and/or to the walls of the vessel, thereby preventing and/or minimizing potential damage to the vasculature itself.

Regarding the pressure-wave reflective element's ability to reflect and/or re-directs at least a portion of the pressure waves toward the guidewire lumen and/or guidewire to excite and/or vibrate the guidewire, the pressure waves or portion of the pressure wave(s) that does not pass through the pressure-wave reflective element may be reflected and/or re-directed by the pressure wave reflective element toward the guidewire lumen and/or guidewire to excite and/or vibrate the guidewire, as discussed herein above.

Regarding the pressure-wave reflective element's ability to reinforce the balloon, the pressure-wave reflective element may reduce or prevent the balloon's ability, particularly the balloon's working length's ability, to expand and contract upon creation of the cavitation bubbles therein. Reducing the balloon's ability, particularly the balloon's working length's ability, to expand and contract upon the formation of cavitation bubbles within the balloon, reduce or prevent the balloon 616 from applying a hydraulic force or pressure to the vascular occlusion and/or to the walls of the vessel.

Figure 7:
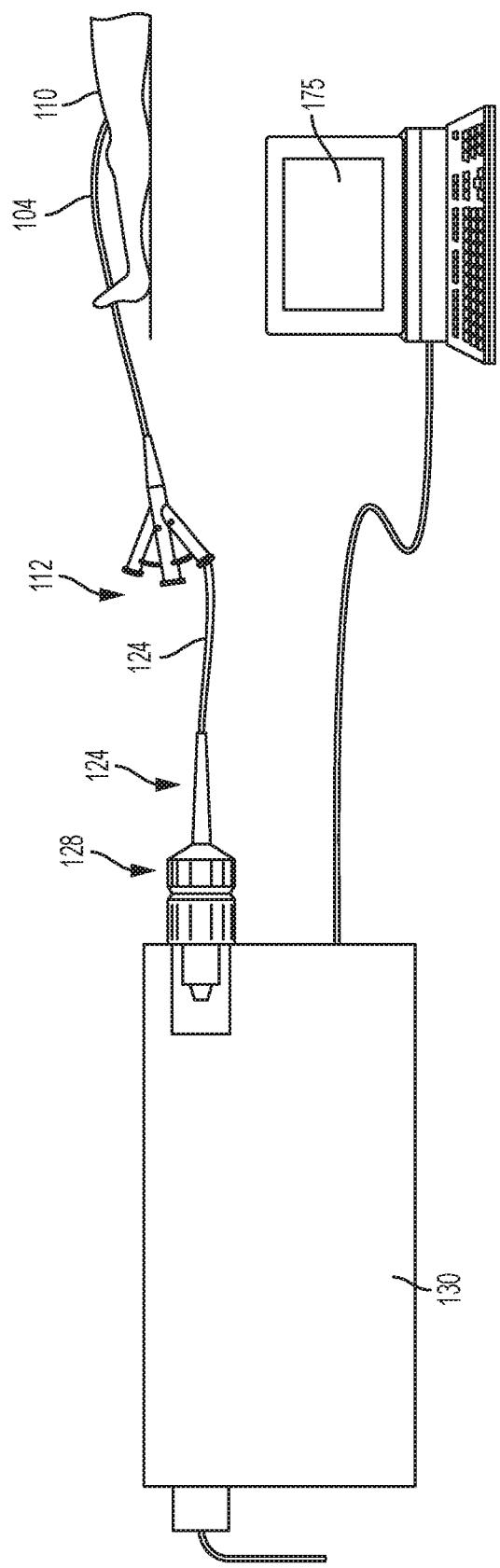
FIG. 7 illustrates an exemplary electrically-induced angioplasty balloon catheter system, including a high voltage pulse generator and an electrically-induced pressure wave emitting balloon catheter.

Referring to FIG. 7, there is depicted an exemplary electrically-induced angioplasty balloon catheter system 100 of the present disclosure. The electrically-induced angioplasty balloon catheter system 100 includes an electrode catheter 124 passing through a proximal hub 112 of a balloon catheter 104, wherein the electrode catheter 124 is coupled to a high voltage pulse generator 90, which is controlled by a generator controller 750. Controller 750 includes one or more computing devices programmed to control the high voltage pulse generator 90. Controller 750 may be internal or external to the high voltage apparatus 90, which produced electrical pulses.

The high voltage pulse generator 90 is connected to the proximal end of the electrode catheter 124 via coupler 128. And the high voltage pulse generator 90 is connected to generator controller 750. The high voltage pulse generator 90 generator 750 and/or generator controller 750 of FIG. 7 includes a non-transitory computer-readable medium (for example, memory) that includes instructions that, when executed, cause one or more processors to control the high voltage pulse generator 90 and/or other components of the electrically-induced angioplasty balloon catheter system 100. Controller 750 includes one or more input devices to receive input from an operator. Exemplary input devices include keys, buttons, touch screens, dials, switches, mouse, and trackballs which providing user control of generator 750. Controller 750 further includes one or more output devices to provide feedback or information to an operator. Exemplary output devices include a display, lights, audio devices which provide user feedback or information.

FIG. 7 depicts the electrically-induced angioplasty balloon catheter 100 entering the leg, preferably through the femoral artery, of the human body. As discussed above, it may be desirable to treat either CAD or PAD. After entering the femoral artery, the catheter 104 will be directed through the patient's vasculature system and to the coronary arteries to treat CAD. Alternatively, if the catheter 100 is intended to treat PAD, the catheter 100 will be directed through the patient's vasculature system and to the peripheral arteries, such as the vasculature below the knee, particularly the vasculature in the patient's legs and/or feet. Unlike balloon catheters, the catheter 100 of the present disclosure is able to more easily navigate and enter smaller sized vasculature because the overall diameter of the sheath is smaller in comparison to balloon catheters, thereby allowing the catheter 100 of the present disclosure more easily treat PAD. That is, the increased size of a balloon of an electrically-induced angioplasty balloon catheter and/or a typical dilation balloon catheter (in comparison to the catheter 100 of the present disclosure) may prevent or increase the difficulty of the balloon-type catheter from entering, penetrating and/or treating the peripheral vasculature, such the vasculature below the knee in the legs and/or feet.

Figure 8:
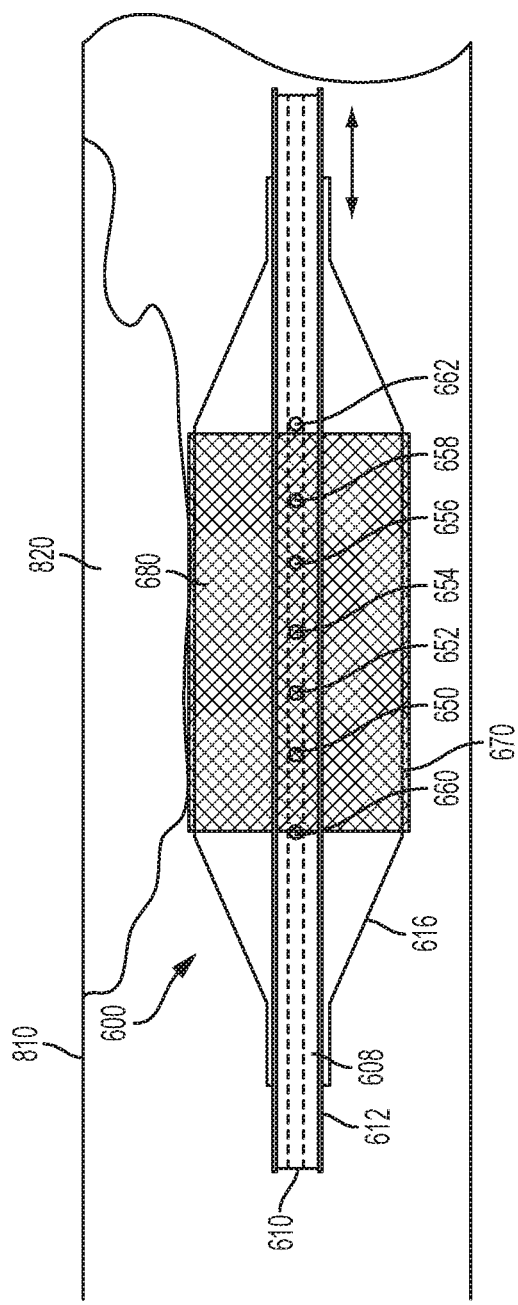
FIG. 8 is a representative longitudinal view of the distal end of an electrically-induced angioplasty balloon catheter adjacent to a vascular obstruction within a vessel of a subject, according to one variation of the present disclosure.

Referring to FIG. 8, there is depicted the as discussed above, upon the electrode assemblies 650, 652, 656 creating an electrical arc in the liquid medium and the liquid medium absorbing the electrical energy, a pressure wave is created in the liquid medium, which in turn generates a pressure wave and cavitation bubbles are produced. The pressure waves penetrate and/or pass through the balloon assembly 616, and the formation of the cavitation bubbles expands the diameter of the balloon assembly. Referring again to FIG. 3, as the liquid medium absorbs the electrical energy, the pressure waves 98 (dotted lines) propagate through the liquid medium and through the balloon assembly 116. Upon passing through the balloon assembly 116, the resultant energy of the pressure waves 98 transferred to the vascular obstruction 820 and/or to the walls of the vessel 810, as seen in FIG. 8. The transfer of the energy produced by the pressure waves 98 to the vascular obstruction 820 and/or to the walls of the vessel 810 is sufficient to disrupt intraluminal as well as medial (within the tissue layer of the vascular wall) vascular obstructions (for example, calcium deposits). The forces generated by the pressure waves 98 can propagate radially, including in forward (such as, parallel to the vessel), upward (such as, perpendicular to the vessel), and backward (such as, proximally) directions. Pressure waves produced in this manner can also be used to increase vessel compliance prior to performing another procedure, such as a traditional balloon angioplasty.

Again, upon introducing the electrical into the liquid medium and the liquid medium absorbing the electrical energy or pulse, a pressure wave in the liquid medium is not only produce, but cavitation bubbles are created. The cavitation bubbles created within the balloon assembly 116 cause the balloon assembly 116 to expand and contract. The expansion and contraction of the balloon assembly 116 creates a hydraulic force that is also transferred to the vascular obstruction 820 and/or to the walls of the vessel 810 is sufficient to disrupt intraluminal as well as medial (within the tissue layer of the vascular wall) vascular obstructions (for example, calcium deposits).

Additionally or alternatively, the catheter of the present disclosure can also be used to deliver one or more therapeutic agents to the vascular obstruction 820 and/or to the vascular tissues of the vessel 810. The outwardly propagating pressure waves 98 generated by the absorption of the electrical energy by the liquid medium and/or the rapid expansion and contraction of the balloon assembly 150 can deliver one or more therapeutic agents that have been coated, for example, on the outside of the balloon assembly 116. When the balloon assembly 116 is brought in contact with the desired target (for example, a vascular obstruction 820 and/or the vascular tissues of the vessel 810), the propagation of the pressure waves 98 through the balloon assembly 116 and/or the expansion and contraction of the balloon assembly 116 causes the therapeutic agent to become detached from the balloon assembly 116 and be delivered to or embedded in the desired target. The resultant pressure waves enhance the delivery of the therapeutic agent. Additionally, under suitable therapeutic parameters, the pressure waves 98 can create small spaces within the vascular obstruction 820 and/or within the vascular tissues of the vessel 810, which enhances the penetration of the therapeutic agent into the vascular obstruction 820 or the vascular tissue of the vessel 810. Energy from the pressure waves 98 also increases the kinetic energy of the molecules making up the therapeutic agents, which further enhances the delivery and penetration of the therapeutic agent into the target tissue.

The therapeutic agents of the present disclosure can be chosen based upon functional characteristics, including, but not necessarily limited to, the ability to inhibit restenosis, mitosis or cellular proliferation. For example, a therapeutic agent can be a taxane, including paclitaxel, docetaxel, protaxel, DHA-paclitaxel, PG-paclitaxel, docosahexaenoic acid (DHA), or any combinations or derivatives thereof capable of inhibiting mitosis or cellular proliferation. In some cases, the presence of a mitotic inhibitor prevents restenosis that may occur in the absence of the inhibitor. Other examples of therapeutic agents include rapamycin (for example, sirolimus) or a derivative of rapamycin (for example, everolimus), or any combinations or derivatives thereof. Additionally or alternatively, specific inhibitors of neovascularization such as thalidomide, statins such as atorvastatin, cerivastatin, fluvastatin, or anti-inflammatory drugs like corticoids or lipophilic derivatives of corticoids such as betamethasone diproprionate or dexa-methasone-21-palmitate are examples of oxidation-insensitive drugs that can be used with the catheters of the present disclosure. Various therapeutic agents may be applied or combined if different pharmacological actions are required or efficacy or tolerance is to be improved.

The therapeutic agents can also be combined with various adjuvants and excipients to enhance efficacy or delivery of the therapeutic agents. For example, the therapeutic agents can be combined with lipophilic antioxidant such as nordihydroguaiaretic acid, resveratrol and propyl gallate to enhance the adhesion of the therapeutic to, for example, a balloon assembly. In some cases, the combination of a therapeutic agent such as paclitaxel and a lipophilic antioxidant such as nordihydroguaiaretic acid can be applied to a balloon assembly without the need for additional polymers (such as, polymer-free).

The total number of pulses administered during a particular treatment period depends on a variety of factors, including patient characteristics, the type of condition being treated, and the specific characteristics of the vascular obstruction, as one of ordinary skill in the art would readily appreciate based on the present disclosure. In some cases, the total number of pulses administered during a treatment period can range from a single pulse to any number of pulses generated in a 10 second treatment period, a 15 second treatment period, a 20 second treatment period, a 25 second treatment period, a 30 second treatment period, up to a 1 minute treatment period. Treatment periods can be repeated depending on the extent of the vascular obstruction remaining after initial treatment.

The degree of force generated by the pressure waves 98 can be modulated by using electrical generators that produce electrical energy at different voltage levels and/or at different pulse durations, as would be appreciated by one of ordinary skill in the art based on the present disclosure. For example, different degrees of force may be required to break apart a vascular obstruction, as compared to the degree of force required to deliver a therapeutic agent to vascular tissue. The force generated by the pressure waves 98 can also obviate the need to inflate the balloon assembly 116 to the high pressures typically required to treat effectively a subject during angioplasty or other balloon procedures (for example, 14-16 atmospheres). In some cases, the balloon assembly 150 of the present disclosure can be inflated with liquid medium 160 to pressures greater than 0 atmospheres to about 20.0 atmospheres. In some cases, the balloon assembly 150 of the present disclosure can be inflated with liquid medium 160 to pressures between about 1.0 atmosphere to about 10.0 atmospheres. In other cases, the balloon assembly 150 of the present disclosure can be inflated with liquid medium 160 to about 0.5, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0 atmospheres. The use of dilation balloon assemblies 150 at low pressures can reduce the potential for damaging healthy vascular tissue during a procedure, and can facilitate the treatment of a greater range and types of vascular obstructions.

Referring again to FIG. 8, there is depicted a representative longitudinal view of the distal end of the electrically-induced angioplasty balloon catheter 600 of FIG. 6 adjacent to a vascular obstruction 820 within a vessel 810 of a subject. The balloon catheter 600 has been placed at the desired location by sliding the catheter 600 over a guidewire 610 through the guidewire lumen 610 of the catheter sheath 608. The catheter sheath 608 includes the radiopaque marks 660, 662 and the electrode assemblies 650, 652, 654, 656, 658. The catheter sheath 608 is inserted into catheter sheath 612, which is coupled to the proximal and distal ends of the balloon 616, and positioned by the clinician in a position such that the radiopaque marks 660, 662 align with the ends of the working length 670 of the balloon 616 and the electrode assemblies 650, 652, 654, 656, 658 are within the working length 670 of the balloon 616. That is, the electrode catheter, particularly the catheter sheath 608, is slidable within catheter sheath 612. Although FIG. 8 illustrates the catheter sheath 608 slidable within the catheter sheath 612, the arrangement could be reversed such that the catheter sheath 612 is slidable within the catheter sheath 608.

The catheters of the present disclosure may also include one or more radiopaque markers positioned on the balloon assembly (for example, marking the proximal and distal ends of the balloon assembly) in order to assist with the placement of the distal end of the catheter at the desired location within the subject's vessel prior to the commencement of a procedure. The catheters of the present disclosure may also include one or more radiopaque markers positioned at and/or near the electrode assemblies in order to assist with the placement of the electrode assemblies within the balloon assembly, for example, such that the electrode assemblies are positioned adjacent to a vascular obstruction prior to the commencement of a procedure. Radiopaque markers can be made of any suitable materials known in the art, including but not limited to, platinum, iridium, and alloys thereof.

Figure 9:
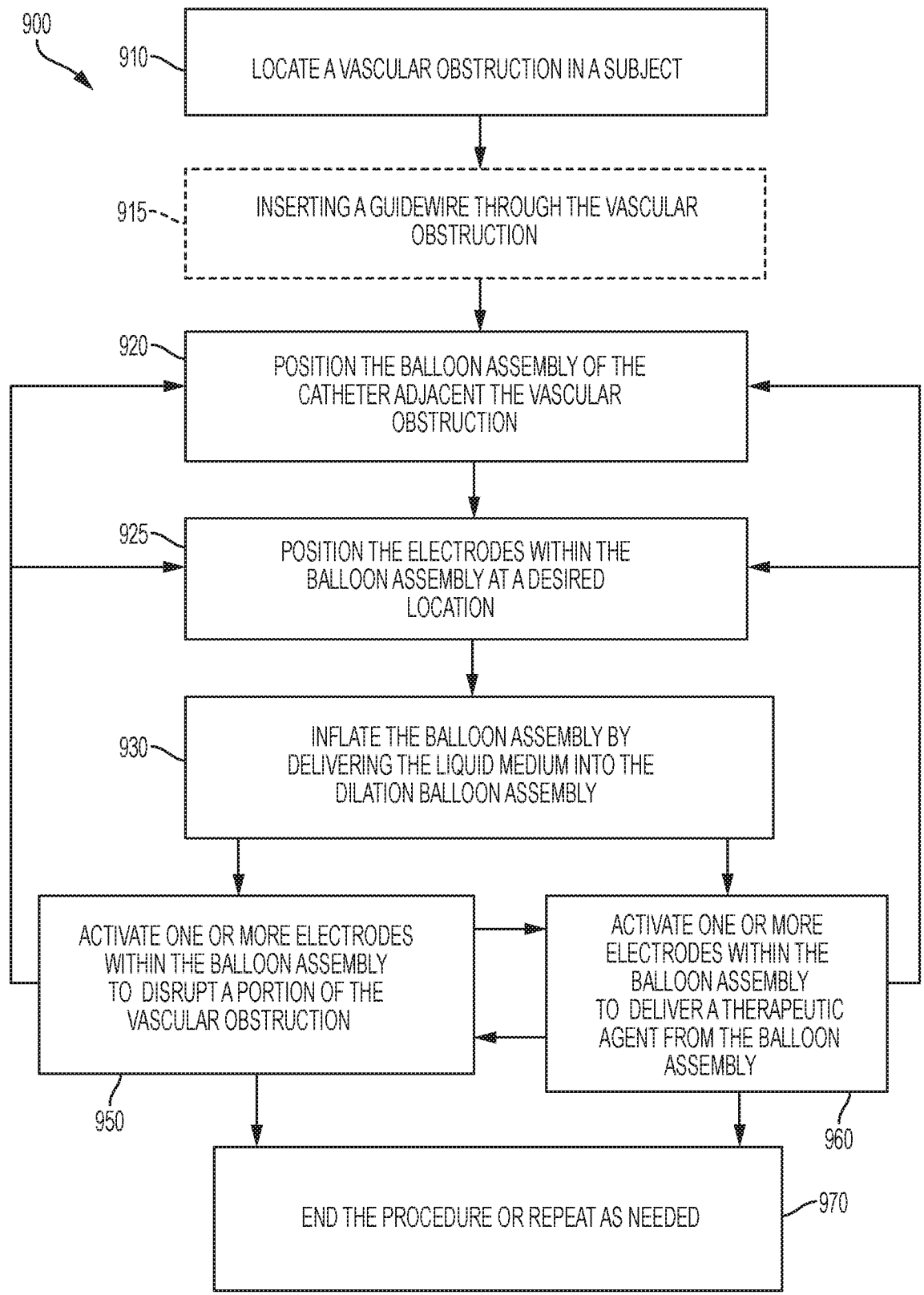
FIG. 9 is a representative flow diagram of methods of treating a subject using an electrically-induced angioplasty balloon catheter, according to one embodiment of the present disclosure.

Referring to the flow chart in FIG. 9, the present disclosure includes a method for treating a subject with a vascular obstruction 900 using embodiments of the catheter described herein. Although it is not illustrated in FIG. 9, it may be desirable to use an atherectomy device, such as an ablation device, including a laser catheter to ablate at least a portion of the vascular occlusion in the vessel of the subject prior to performing the method set forth in FIG. 9 and/or using the laser catheter to ablate at least a portion of the vascular occlusion in the vessel prior to and/or subsequent to performing any of the steps set forth in FIG. 9. The method 900 in FIG. 9 includes locating a vascular obstruction in the vessel of a subject 910. The next step, which is optional, includes locating a guidewire at the occlusion and/or inserting a guidewire through the occlusion 915. Thereafter, any of the embodiments of the electrically-induced angioplasty balloon catheter 100 described herein may be slid over the guidewire and into the vasculature such that the balloon assembly 616, which is coupled to the catheter 100, is positioned adjacent to the vascular obstruction 920. As discussed herein, the electrode assemblies 650, 652, 654, 656, 658 within the balloon assembly 616 may be fixed or slidable with respect to the balloon assembly 616 because the electrode assemblies may be disposed on an electrode catheter sheath 610 that is fixed or slidable with respect to the balloon assembly 616 and catheter sheath 612 to which the balloon 616 is attached. For example, if the electrode assemblies are included with the electrode catheter 610, which is slidable within the sheath 612 and balloon assembly 616 of the balloon catheter 600, the electrode assemblies may be positioned (and subsequently re-positioned) anywhere along the length of the balloon 616 at a desired location according to step 925. Additionally or alternatively, the method 900 includes inflating the balloon assembly by delivering the liquid medium (for example, contrast medium) from the inner lumen of the catheter through one or more liquid medium ports and into the balloon assembly 930. In some cases, the method 900 includes activating at least one electrode assembly enclosed within the balloon assembly to produce electrical arcs into and/or to react with the liquid medium to produce propagating pressure waves and disrupt a portion of the vascular occlusion 950. In some cases, the method 900 includes activating at least one electrode assembly enclosed within the balloon assembly to create and deliver electrical energy into and/or to react with the liquid medium to produce propagating pressure waves to deliver a therapeutic agent to the vascular obstruction and/or the vascular tissue near the obstruction 960.

Although the method illustrated in FIG. 9 depicts step 920, which includes positioning the balloon assembly adjacent the vascular occlusion, being performed prior to step 925, which includes positioning the electrodes within the balloon assembly at a desired location, step 925 may be performed after or in parallel with step 920. Additionally, although the method illustrated in FIG. 9 depicts step 920 and step 925 as occurring prior to step 930, which includes inflating the balloon assembly with liquid medium, step 930 may be performed prior to or in parallel with one or both of step 920 or step 925. That is, steps 920, 925 and 930 may be performed in any order.

Activating an electrode assembly to disrupt a portion of a vascular obstruction and/or to deliver a therapeutic agent can be performed in any sequence, if at all, as part of the method 900. For example, step 950 could be performed without performing step 960, step 960 could be performed without performing step 950, step 950 could be performed serially while performing step 960, such that step 950 is performed firstly and step 960 is performed secondly, step 950 could be performed serially while performing step 960, such that step 960 is performed firstly and step 950 is performed secondly, or steps 950 and 960 could be performed in parallel. Upon completing step 950 and/or step 960, the balloon assembly can optionally be repositioned within the vasculature and adjacent another portion thereof. Similarly, upon completing step 950 and/or step 960, the electrode assemblies can optionally be repositioned within the balloon assembly. Either or both the balloon assembly can be repositioned within the vasculature or the electrode assemblies within the balloon assembly can be repositioned. The method 900 also includes ending the procedure when the desired therapeutic outcome is obtained, or repeating any of 910 through 950, 960 as may be necessary to treat a subject having a vascular obstruction. Furthermore, if step 960 is not performed in the method depicted in FIG. 9, a drug eluting (coated) balloon (DEB or DCB) catheter may be used to deliver drugs to the remnants of the vascular occlusion. Disrupting the vascular occlusion with the pressure waves prior to utilizing a DEB may increase the effectiveness of the drugs being applied to the vascular occlusion because to the pressure waves disrupt the intraluminal as well as medial (within the tissue layer of the vascular wall) vascular obstructions (for example, calcium deposits), thereby creating a pathway for the drug to enter the intraluminal and medial portions of the vasculature and/or vascular occlusion.

Additionally or alternatively, methods of the present disclosure also include activating at least one electrode assembly enclosed within the balloon assembly to produce pulses of electrical energy to react with and/or to react with the liquid medium and propagating pressure waves to assist in stent deployment. Cavitation bubbles generated by pulsing electrical energy, which reacts with the liquid medium and can assist in seating or expanding the stent to its full diameter as part of a medical procedure.

Traditional balloon catheter typically includes a two-sheath construction such that an inner sheath is disposed within an outer sheath, and the inner sheath extends beyond the distal end of the outer sheath. A balloon is coupled to the inner sheath and outer sheath. Incorporating an electrode catheter between the inner sheath and outer sheath of a balloon catheter, however, increases the overall size and diameter of the balloon catheter, thereby potentially limiting the ability of the balloon catheter to reach and treat smaller sized vessels, such as peripheral arteries below the knees, particularly those arteries located with the feet. It is, therefore, desirable to reduce the overall size and diameter of the balloon catheter, including the size and diameter of the sheath(s) and/or the balloon. Reducing the overall size and diameter of the balloon catheter will, therefore, increase the balloon catheter's ability to reach and treat smaller sized peripheral arteries and other smaller sized vasculature.

One potential solution for reducing the overall size and diameter of the balloon catheter is to remove the inner sheath, which will allow the balloon and outer sheath (now just one sheath) to be sized smaller. Removing the inner sheath, however, removes (a) the lumen through which the guidewire travelled and (b) the component to which the balloon was coupled and (c) the ability to sealing the inflation fluid used to inflate the balloon. What is, therefore, needed is a means for coupling the distal portion of the balloon while allowing a guidewire to pass therethrough and for providing a seal with the guidewire upon introduction of the inflation fluid into the balloon.

Figure 10:
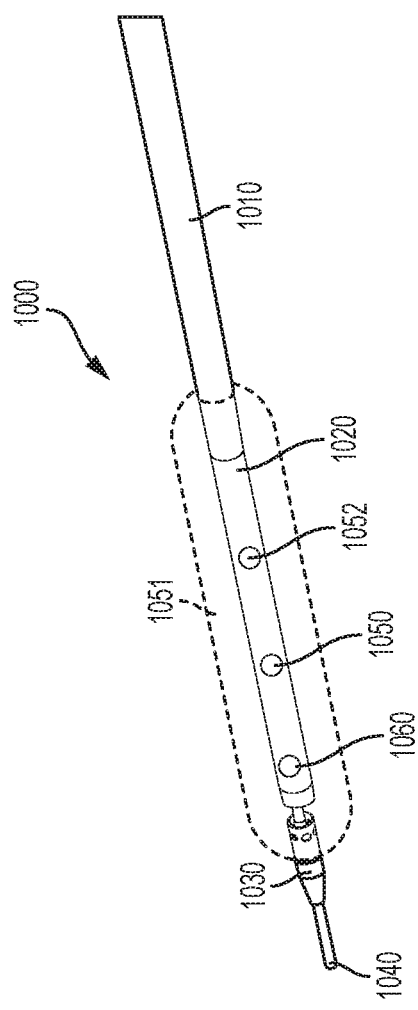
FIG. 10 is a representative perspective view of the distal end of a balloon catheter with an electrode catheter slidable within the balloon and balloon catheter, according to one embodiment of the present disclosure.
Figure 10A:
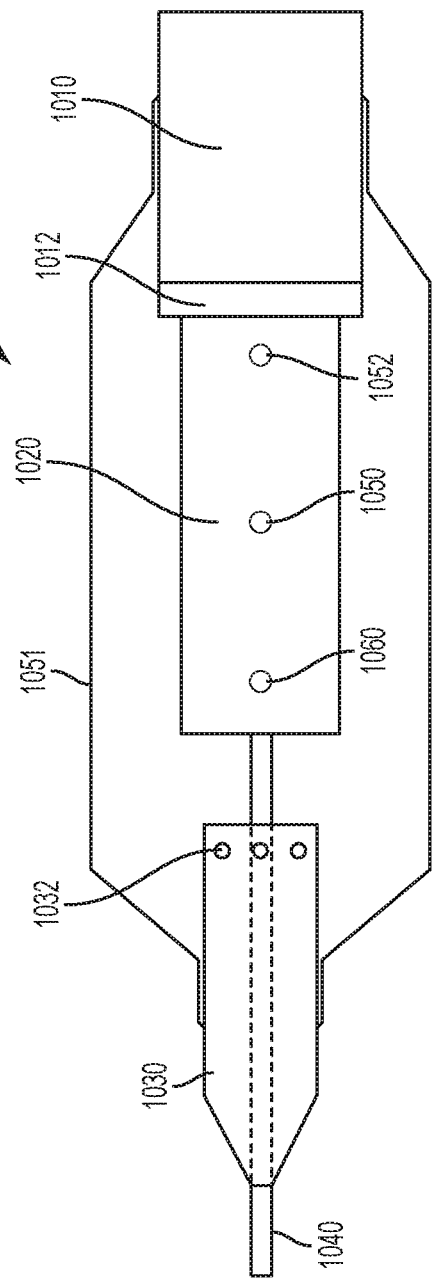
FIG. 10A is a representative cross-sectional side view of the distal end of the balloon catheter and electrode catheter illustrated in FIG. 10.
Figure 10B:
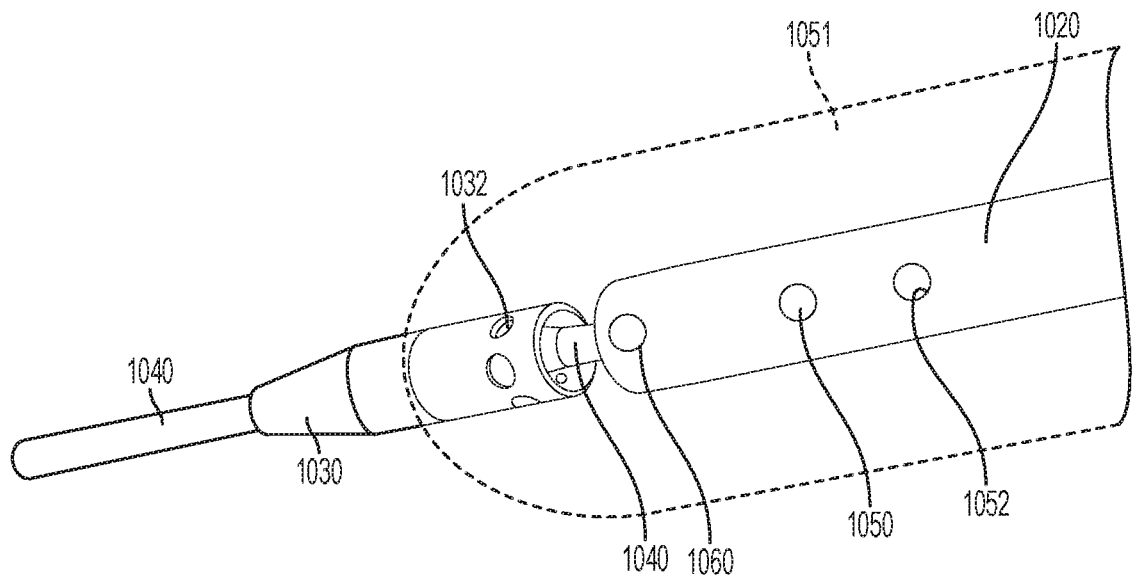
FIG. 10B is an enlarged representative perspective view of the distal end of the balloon catheter and electrode catheter illustrated in FIG. 10, wherein a sealable valve is illustrated at the distal end of the balloon.

Referring to FIGS. 10 and 10A and 10B, there is depicted the distal end of an alternative system for treating an obstruction within vasculature of a subject that includes such a means and omits a stationary inner sheath, which is typically included within a traditional balloon catheter. The system comprises a catheter 1000 and an electrode catheter (or sheath) 1020 insertable and slidable within the catheter 1000. The catheter 1000 includes a sheath 1010 with a lumen (not shown) extending form its proximal end to its distal end, a tip 1030, and a balloon 1051 coupled to the tip 1030 and a distal portion of the sheath 1010. The catheter 1000 does not include a sheath (with a lumen) extending between the distal end of the sheath 1010 and the proximal end of the tip 1030 within the balloon. The system further comprises an electrode catheter 1020 comprising a radiopaque marker 1060 at the distal end of the electrode catheter 1020 and one or more electrode assemblies 1050, 1052 along the length of the electrode catheter 1020. The one or more electrode assemblies 1050, 1052, which is coupled to a high voltage pulse generator, are as discussed hereinbefore.

Figure 11:
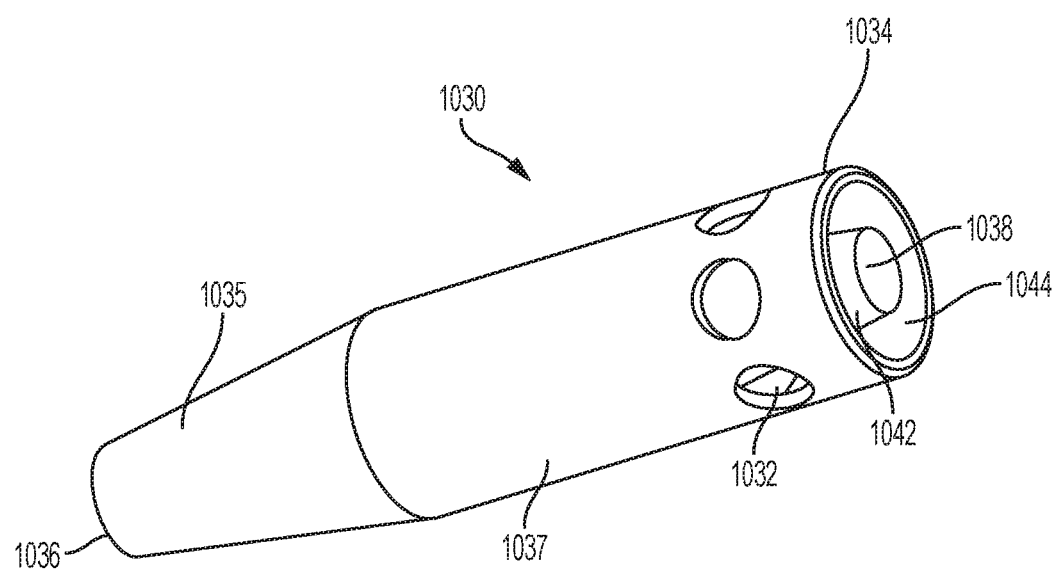
FIG. 11 is an enlarged representative perspective view of the sealable valve depicted in FIGS. 10, 10A and 10B.
Figure 11A:
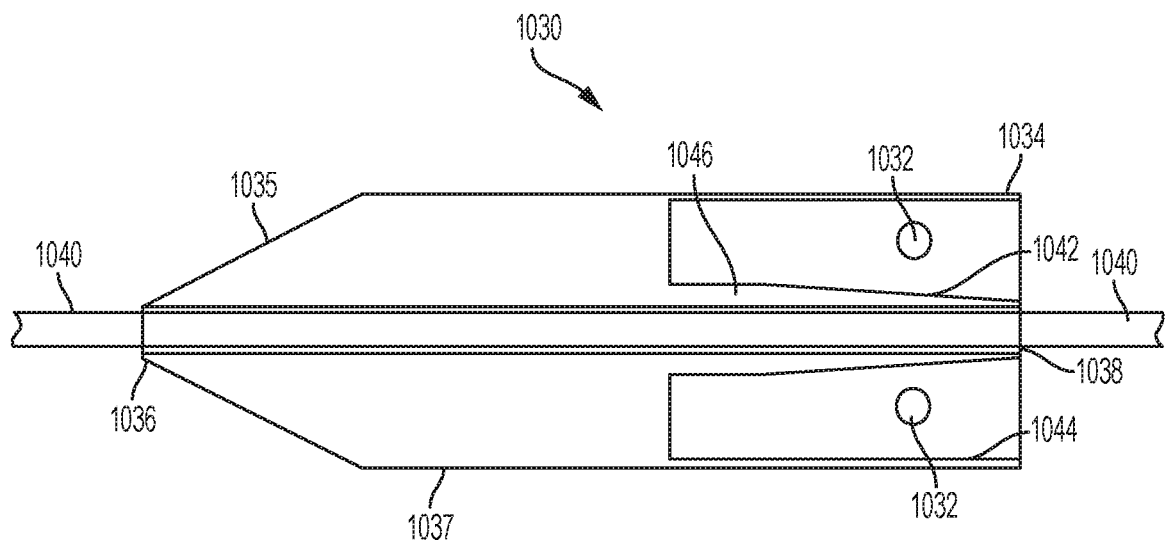
FIG. 11A is an enlarged representative cross-sectional side view of the sealable valve in an unsealed configuration with respect to a guidewire.
Figure 11B:
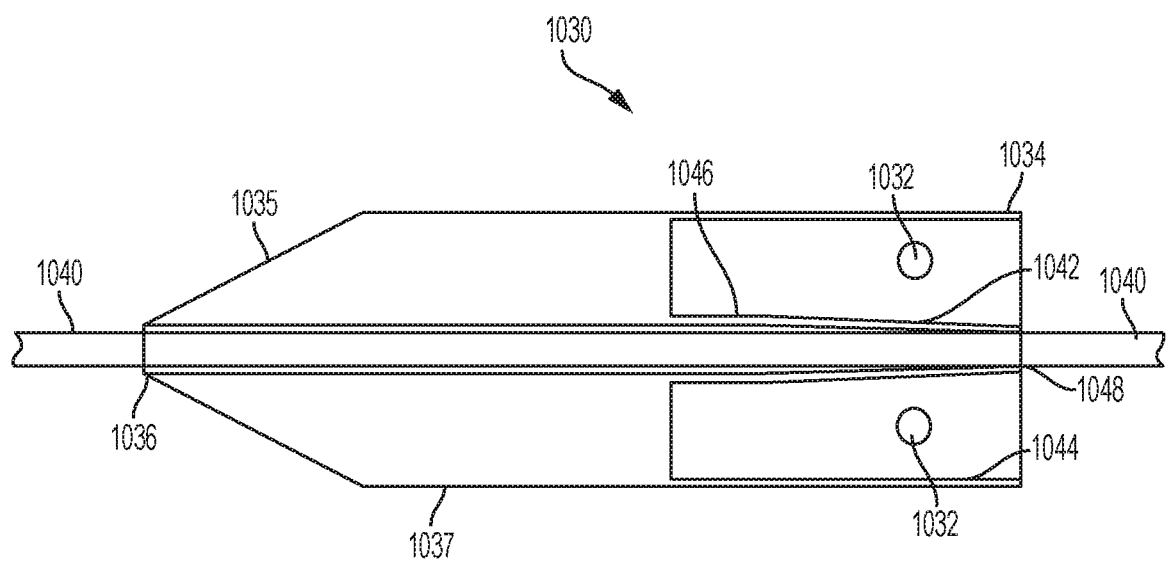
FIG. 11B is an enlarged representative cross-sectional side view of the sealable valve in a sealed configuration with respect to a guidewire.

Referring to FIGS. 11, 11A, and 11B, the tip 1030 includes a proximal end 1034, a distal end 1036 and a lumen 1038 extending therethrough from its proximal end 1034 to its distal end 1036. The tip 1030 includes a valve that seals the intersection of the tip 1030 and the guidewire 1040 as the guidewire 1040 passes through the guidewire lumen 1038. One example of a valve is that which is depicted in FIGS. 11, 11A, and 11B which illustrate a flange 1046 that is disposed at and/or toward the proximal end 1034 of the tip 1030.

Referring back to FIGS. 10, 10A, and 10B, the balloon 1051 is coupled to the distal end of the sheath 1010 and the tip 1030. Upon introducing the guidewire 1040 through the lumen of the sheath 1010 and into the guidewire lumen 1038 of the tip, the sheath 1010 and tip 1030 are slidably coupled such that the sheath 1010 and tip 1030 can slide over the guidewire 1040, as depicted in FIG. 11A. As illustrated in this figure, there is a gap (or opening) caused by the guidewire lumen 1038 between the flange 1046 and the guidewire 1040. If the gap is maintained during introduction of the inflation fluid into the balloon 1051, the inflation fluid would travel through the guidewire lumen 1038 and into the patient's vasculature, which may be undesirable. The flange 1046, which may include a tapered portion 1042 that tapers from the tip's distal end toward its proximal end, is configured to radially collapse upon introduction of the inflation fluid into the balloon 1051 due to the increased fluid pressure on the flange 1046. The increased fluid pressure on the flange 1046 actuates the flange 1046 and moves it radially inward toward the guidewire lumen 1038 such that the gap between flange 1046 and the guidewire 1040 closes, thereby creating a seal between the between flange 1046 and the guidewire 1040, as depicted in FIG. 11B. The reduced thickness of the tapered portion 1042 of the flange 1046 as the flange 1046 tapers radially inward towards the guidewire lumen 1038 as the flange 1046 progresses from the distal end 1036 toward the proximal portion 1034 increases the flange's ability to flex upon exposure to the pressure created upon introduction of the inflation fluid. Upon removal of the inflation fluid from the balloon 1051, the pressure within the balloon 1051 decreases, the pressure on the flange 1046 decreases, and the flange 1046 naturally retracts to its original position as depicted in FIG. 11A, thereby reestablishing the gap between the tip 1030 and the guidewire 1040 so that the two components may slide with respect to one another. Accordingly, the flange 1046 acts as sealable valve within the tip 1030, and the flange 1046 is actuated with the introduction and removal of the inflation fluid into and from the balloon 1051.

Although the tapered portion 1042 illustrated in FIGS. 11A and 11B tapers from the tip's distal end toward its proximal end, the direction of the taper may be reversed such that the tapered portion tapers from the tip's proximal end toward its distal end. Additionally, the flange 1046 may taper towards any portion along its length such that a portion of the flange is thinner at one or more locations along its length in comparison to other locations along its length. Accordingly, upon an increased fluid pressure being imparted on the flange 1046, thinner portion of the flange 1046 actuates and moves radially inward toward the guide-wire lumen 1038 such that the gap between flange 1046 and the guidewire 1040 closes, thereby creating a seal between the between flange 1046 and the guidewire 1040.

FIGS. 10, 10A, 10B, 11, 11A, and 11B, do not illustrate an inflation lumen through which the inflation fluid is introduced and removed from the balloon. Nevertheless, the sheath 1010 may also include a separate inflation lumen (not shown) integrally located within the structure of the sheath 1010 itself or the inflation fluid may be introduced into the balloon 1051 through an opening (or gap) between the electrode catheter 1020 and the sheath 1010. For the purposes of this disclosure, the inflation shall include both the separate inflation lumen integrally located within the structure of the sheath 1010 itself and an opening (or gap) between the electrode catheter 1020 and the sheath 1010.

Referring again to FIGS. 11, 11A, and 11B the tip 1030 may be constructed from any type of compressible or compliant biopolymers, such as silicones or fluoro-polymers, compliant adhesives, etc. The configuration of the tip 1030 depicted in these figures includes an exterior wall 1044 and a flange 1046 disposed radially therein, to create a gap therebetween for the inflation fluid to enter and actuate the flange 1046. The flange is also depicted as being disposed toward the proximal end 1024 of the tip 130, which itself is depicted as tubular, and its distal end has an inward taper that tapers distally from the exterior wall 1044 towards the guidewire lumen 1038. Although the tip 1030 is depicted as including particular components and shapes, the present disclosure shall include other shapes and components known to one of skill in the art. Moreover, the tip may alternatively include a self-sealing tube constructed of any type of compressible or compliant biopolymers, such as silicones or flouro-polymers, compliant adhesives, etc. For example, the tip may include a tube that has a lumen passing therethrough such that upon insertion of a guidewire, the lumen expands, and upon removable of the guidewire, the lumen contracts, thereby appearing as a slit.

As discussed above, omitting a stationary inner sheath form a traditional balloon catheter and including a tip distally disposed from the sheath of the balloon catheter has the advantage of reducing the size of the balloon, and hence smaller sized balloons can enter smaller vessels, particularly peripheral arteries below the knee. Additionally, when a traditional balloon catheter is inflated with liquid, such as saline (and possible with a contrast medium), air may become trapped and unable to escape from the balloon. The tip 1030, particularly the actuation of the flange 1046, which acts as sealable valve within the tip 1030, allows the air initially included within the balloon to escape during inflation, thereby potentially increasing the balloon's ease of use, as well as its effectiveness. For example, during preparation of the balloon, it is common to deflate the balloon, thereby extracting as much air as possible, prior to use. However, it is impractical to remove all of the air during such extraction process. The tip 1030, thereby allows a user to remove more or all air from the balloon during preparation. Additionally, it may not be necessary to deflate the balloon and remove any air prior to use, because the air is allowed to escape during inflation with the liquid.

Continuing to FIGS. 10, 10A, 10B, 11, 11A, and 11B, the tip 1030 may include one or more openings 1032 through its exterior wall 1044. The openings 1032 allow the inflation liquid to reach the flange 1046 not only from the gap between the flange 1046 and the exterior wall 1044 at the proximal end 1034 of the tip 1030 but also at a location distal the proximal end 1034 of the tip 1030. Allowing allow the inflation liquid to reach the flange 1046 at or toward its distal portion, potentially increases the likelihood and effectiveness of actuating the flange 1046. Although the tip 1030 is illustrated as having a tubular section 1037 from its proximal end 1034 and a tapered section 1035 from the end of its tubular section toward the tips distal end 1036, the scope of this disclosure shall include other shapes for the tip.

As discussed herein, as the electrical arc generated by the one or more electrode assemblies 1050, 1052, the electrical arc interacts with the liquid medium, and the liquid medium absorbs the electrical energy, thereby creating cavitation bubbles within the balloon assembly. The openings 1032 within the tip 1030 may reduce the size of the bubble formed within the balloon assembly and/or reduce the likelihood that the bubble will expand toward the distal end of the balloon assembly.

Additionally, although FIGS. 10, 10A, 10B, 11, 11A, and 11B include a tip 1030 included within a balloon catheter that omits a stationary inner sheath, the scope of this disclosure includes utilizing a tip 1030 in a balloon catheter that includes an inner sheath in addition to an outer sheath to which the proximal end of the balloon is attached.

As discussed above, transmitting pulses of electrical energy from an electrode assembly into a liquid medium generates a plurality of propagating pressure waves that cause the balloon assembly, which surrounds the liquid medium, to engage and disrupt at least a portion of the vascular obstruction. The catheter, which the balloon assembly, and the balloon assembly itself, may each include a guidewire lumen through which a guidewire can pass and cross the occlusion. It may also be desirable to excite and vibrate the guidewire to increase the guidewire's ability to pierce and cross the occlusion. Accordingly, the present disclosure also contemplates directing the electrical energy produced by the electrode assembly into the liquid medium in a direction which causes the liquid medium to propagate pressure waves toward the guidewire lumen and/or guidewire such that the pressure waves excite and vibrate the guidewire.

Referring to FIGS. 12A and 12B, an electrically-induced angioplasty balloon catheter system 1210 generally includes an electrode catheter 1212, a guidewire 1214, a sheath 1216, and a handle 1218 that translatably couples the electrode catheter 1212 to a sheath 1216 of a balloon catheter. The electrode catheter 1212, the guidewire 1214, and the balloon catheter, including the sheath 1216 thereof, may be similar to, for example, the components of the two-piece catheter systems or kits described herein. As a specific example, the electrode catheter 1212, the guidewire 1214, and the sheath 1216 may be similar to the components described above in connection with FIGS. 2-11. The electrode catheter 1212 is disposed within a lumen of the sheath 1216 and the handle 1218, and the electrode catheter 1212 includes a proximal coupling 1220 for coupling to the handle 1218. The guidewire 1214 is disposed within a lumen of the electrode catheter 1212. The sheath 1216 includes a proximal coupling 1222 for coupling to the handle 1218. The sheath 1216 also includes a balloon surrounding a portion of the sheath 1216, and the distal end of the sheath 1216 has an opening such that the electrode catheter 1212 enters into the balloon. For example, referring to FIG. 8, item 612 is a sheath, similar to sheath 1216 of FIG. 12A, and item 608 is a sheath for an electrode catheter, and the electrode catheter, including the sheath 608 and electrode assemblies, slide through the sheath 612 and into the opening of the balloon 616.

A liquid medium is introduced into the sheath 1216 distal to the electrode catheter 1212 within the balloon, such that when the electrode assemblies are activated, the liquid absorbs the electrical energy and creates pressure waves and/or cavitation bubbles and resultant pressure waves within the balloon. The liquid is introduced via the lumen or a space between the electrode catheter 1212 and the sheath 1216, which in turn receives the liquid from a proximal port 1224 coupled to the sheath 1616.

Referring now to FIGS. 13A, 13B, 14A-14G, the handle 1218 generally includes a base 1226 that couples to the sheath 1216 and a drive mechanism 1228 that couples to the electrode catheter 1212. As described in further detail below, a portion of the drive mechanism 1628 is translatably coupled to the base 1226 to facilitate translating the electrode catheter 1212 within the lumen of the sheath 1216 and within the balloon. The drive mechanism 1228 may be translated to a proximal position relative to the base 1226 (see FIGS. 13A-13C), a distal position relative to the base 1226 (see FIGS. 13E and 13F), and an infinite number of intermediate positions therebetween (see FIGS. 13D and 13G). As a result, the electrode catheter 1212 may be translated to corresponding positions relative to the sheath 1216 and relative to the balloon.

Figure 14A:
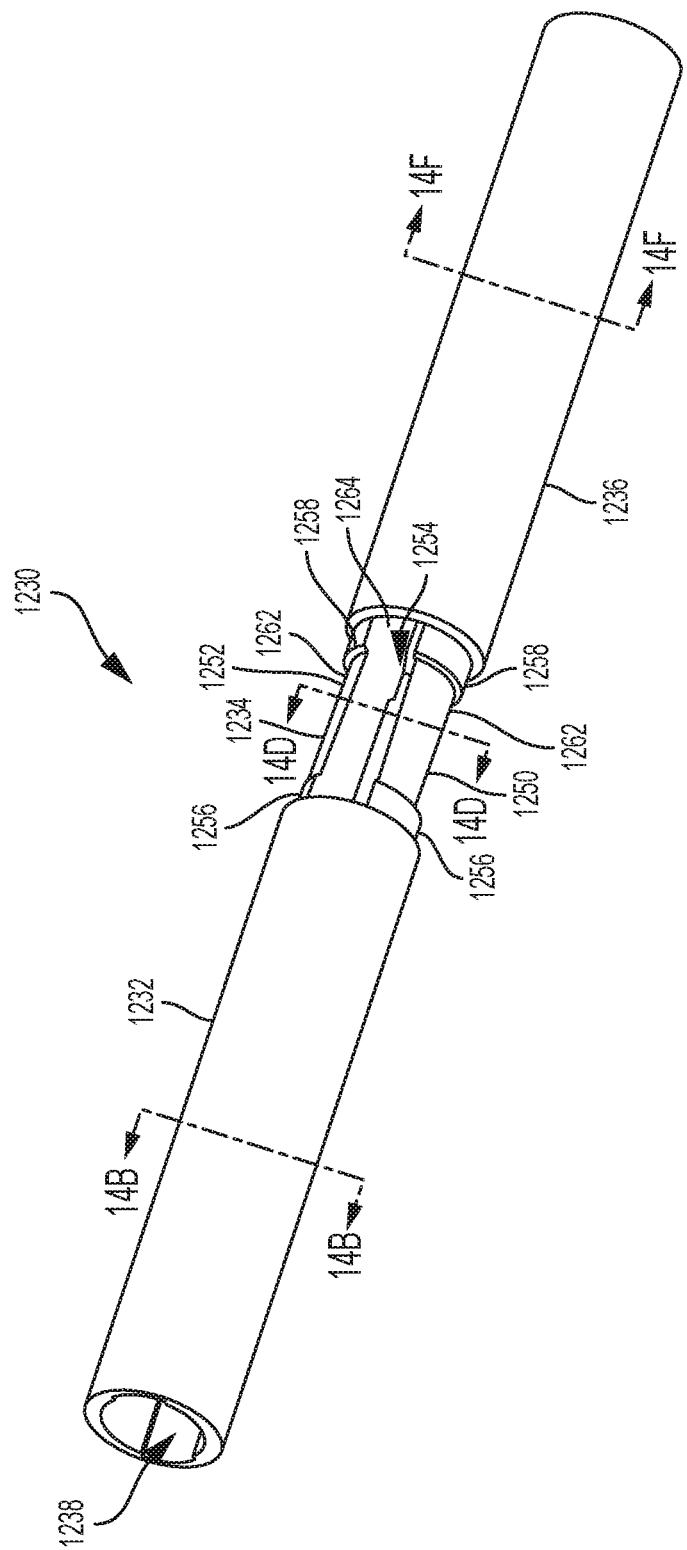
FIG. 14A is a perspective view of a frame of the handle of FIG. 12A.
Figure 14B:
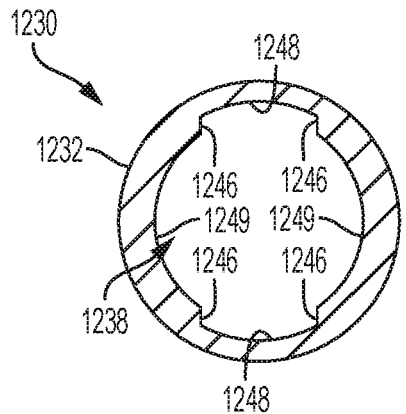
FIG. 14B is an elevation cross-sectional view of the frame along line 16B-12B of FIG. 12A.
Figure 14C:
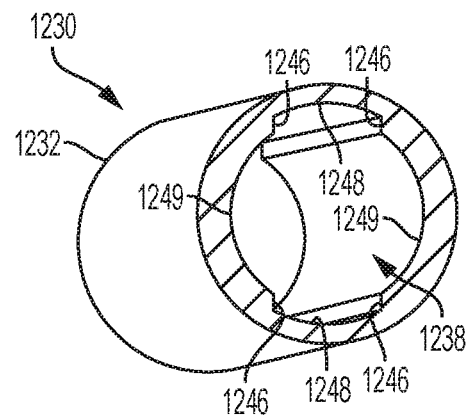
FIG. 14C is a perspective cross-sectional view of the frame along line 12B-12B of FIG. 12A.
Figure 14D:
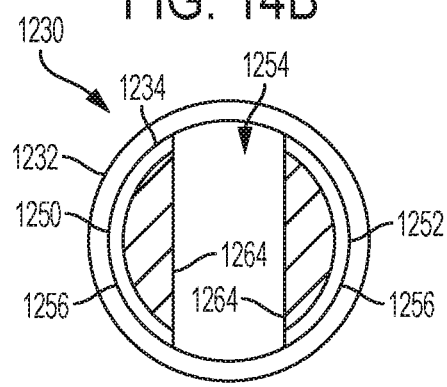
FIG. 14D is an elevation cross-sectional view of the frame along line 12D-12D of FIG. 12A.
Figure 14E:
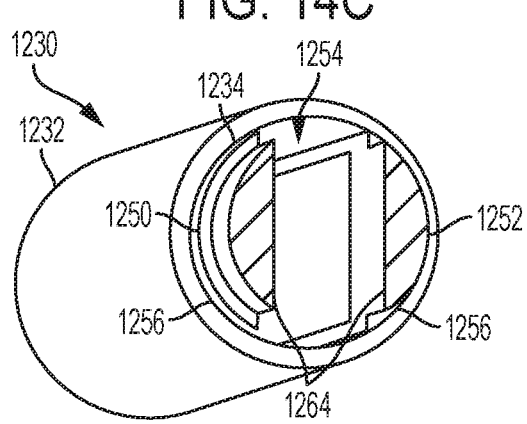
FIG. 14E is a perspective cross-sectional view of the frame along line 12D-12D of FIG. 12A.
Figure 14F:
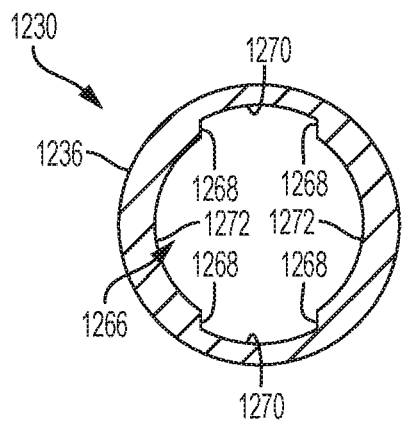
FIG. 14F is an elevation cross-sectional view of the frame along line 12F-12F of FIG. 12A.
Figure 14G:
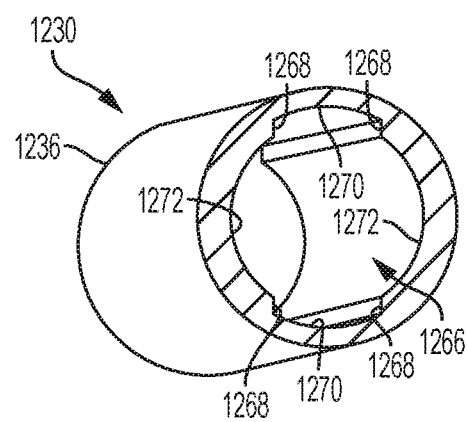
FIG. 14G is a perspective cross-sectional view of the frame along line 12F-12F of FIG. 12A.
Figure 15:
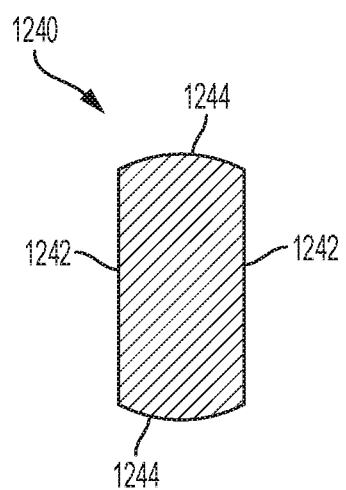
FIG. 15 is an elevation cross-sectional view of the shaft of the handle of FIG. 12A.

Referring now to FIGS. 12A-15, the base 1226 includes an elongated, hollow frame 1230 that movably couples to the drive mechanism 1228. The frame 1230 includes a proximal portion 1232, an intermediate portion 1234, and a distal portion 1236. The proximal portion 1232 defines a proximal passageway 1238 for translatably receiving a shaft 1240 of the drive mechanism 1228 therein. Referring specifically to FIGS. 14B, 14C, and 15, the proximal passageway 1238 may include a first key feature that, by coupling to a second key feature of the shaft 1240, inhibits rotation of the shaft 1240 relative to the frame 1230. For example, the second key feature of the shaft 1240 may be a non-circular cross-sectional area, and the first key feature of the proximal passageway 1238 may be a cross-sectional area that is approximately identical (that is, permitting sufficient clearance to permit relative longitudinal translation, but inhibit relative rotation and transverse translation) to the cross-sectional area of the shaft 1240, or a cross-sectional area that is approximately identical to a portion of the cross-sectional area of the shaft 1240. As a more specific example and as shown in FIGS. 14B, 14C, and 15, the shaft 1240 includes rectangle-like cross-sectional shape, with two opposing flat side surfaces 1242 and two opposing arcuate side surfaces 1244. The proximal passageway 1638 includes a cross-sectional area that is approximately identical to a portion of the cross-sectional area of the shaft 1240. Specifically, the proximal passageway 1238 is defined by four opposing flat side surfaces 1246 and two opposing arcuate side surfaces 1248. The flat side surfaces 1246 and the arcuate side surfaces 1248 engage the flat side surfaces 1242 and the arcuate side surfaces 1244 of the shaft 1240, respectively, to permit relative longitudinal translation, but inhibit relative rotation and transverse translation of the shaft 1240 relative to the frame 1260. In the present example, the proximal passageway 1238 is also defined by two additional opposing arcuate side surfaces 1249 that extend between the flat side surfaces 1246. The arcuate side surfaces 1249 are disposed apart from the shaft 1240 to reduce sliding friction between the shaft 1240 and the frame 1230.

Referring specifically to FIGS. 14A, 14D, and 14E, the intermediate portion 1234 of the frame 1230 includes a first bearing portion 1250, a second bearing portion 1252, and an opening 1254 extending therebetween and aligned with the proximal passageway 1238. Each of the first and second bearing portions 1250, 1252 includes first and second bearing surfaces 1256, 1258. The first and second bearing surfaces 1256, 1258 rotatably support a control element 1260 of the drive mechanism 1228. Each of the first and second bearing portions 1250, 1252 also includes a clearance surface 1262 between the bearing surfaces 1256, 1258. The clearance surface 1262 is also disposed radially inwardly relative to the bearing surfaces 1256, 1258. The clearance surface 1262, together with the opening 1254, facilitates driving engagement of the control element 1260 with the shaft 1240, as described in further detail below. Within the opening 1254, each of the first and second bearing portions 1250, 1252 includes a guide surface 1264. The guide surface 1264 translatably couple to the shaft 1240 and inhibit the shaft 1240 from rotating within the frame 1630.

Figure 13A:
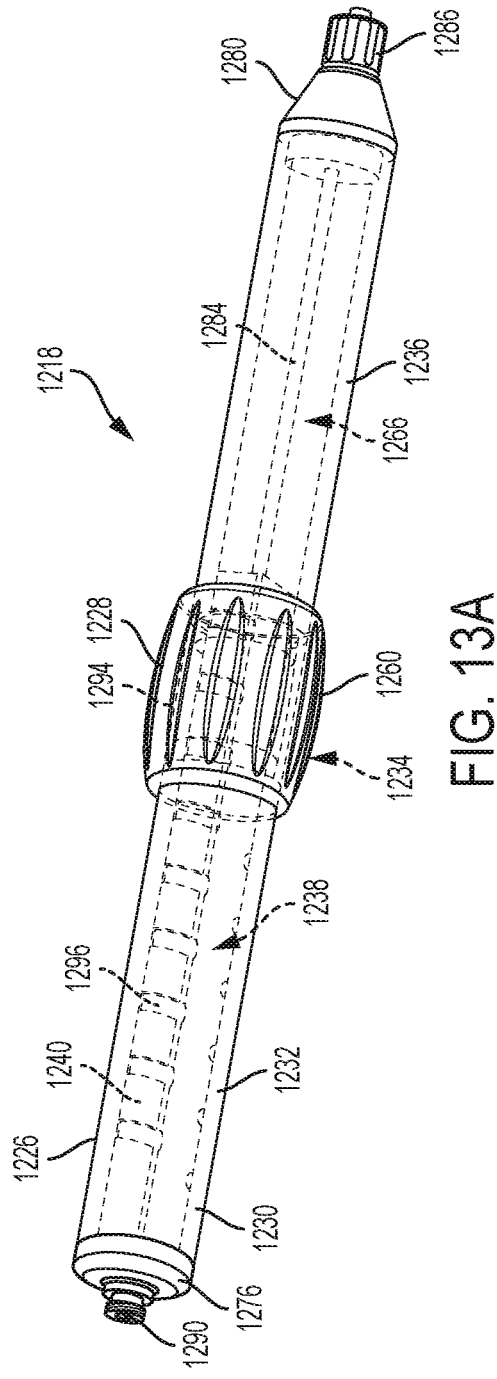
FIG. 13A is a perspective view of the handle of FIG. 12A, wherein several external components are partially transparent to illustrate internal components, and a shaft of the handle is shown in a proximal position.
Figure 13B:
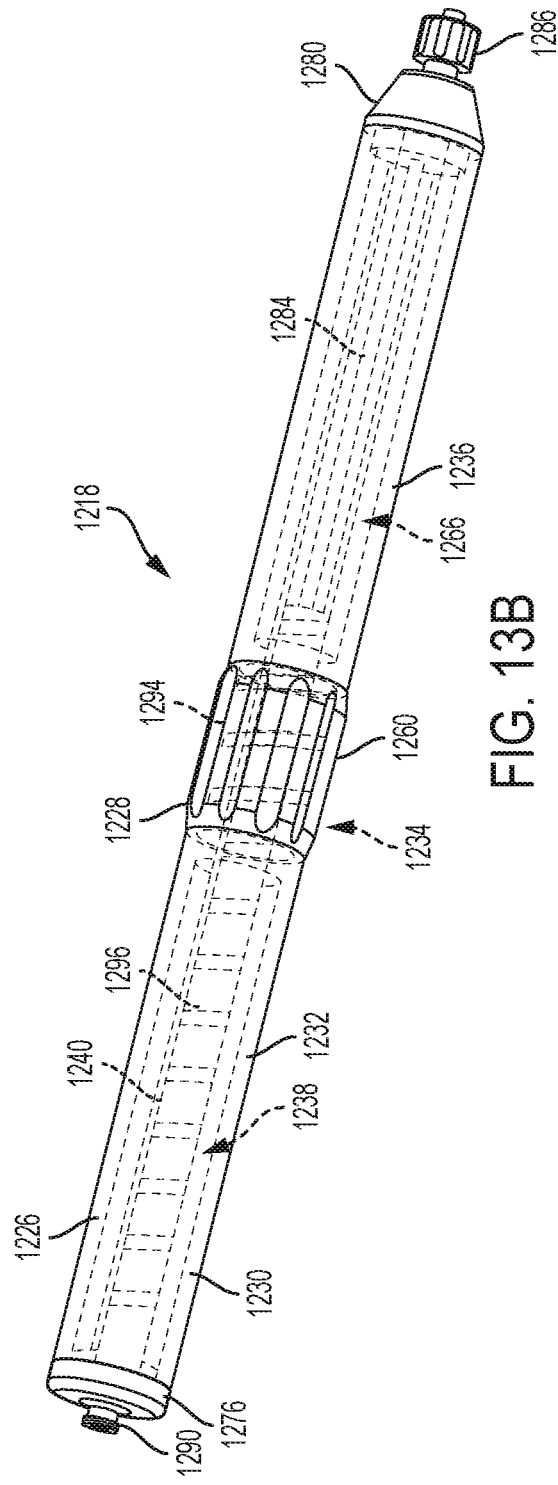
FIG. 13B is another perspective view of the handle of FIG. 12A, wherein several external components are partially transparent to illustrate internal components, and the shaft is shown in the proximal position.
Figure 13I:
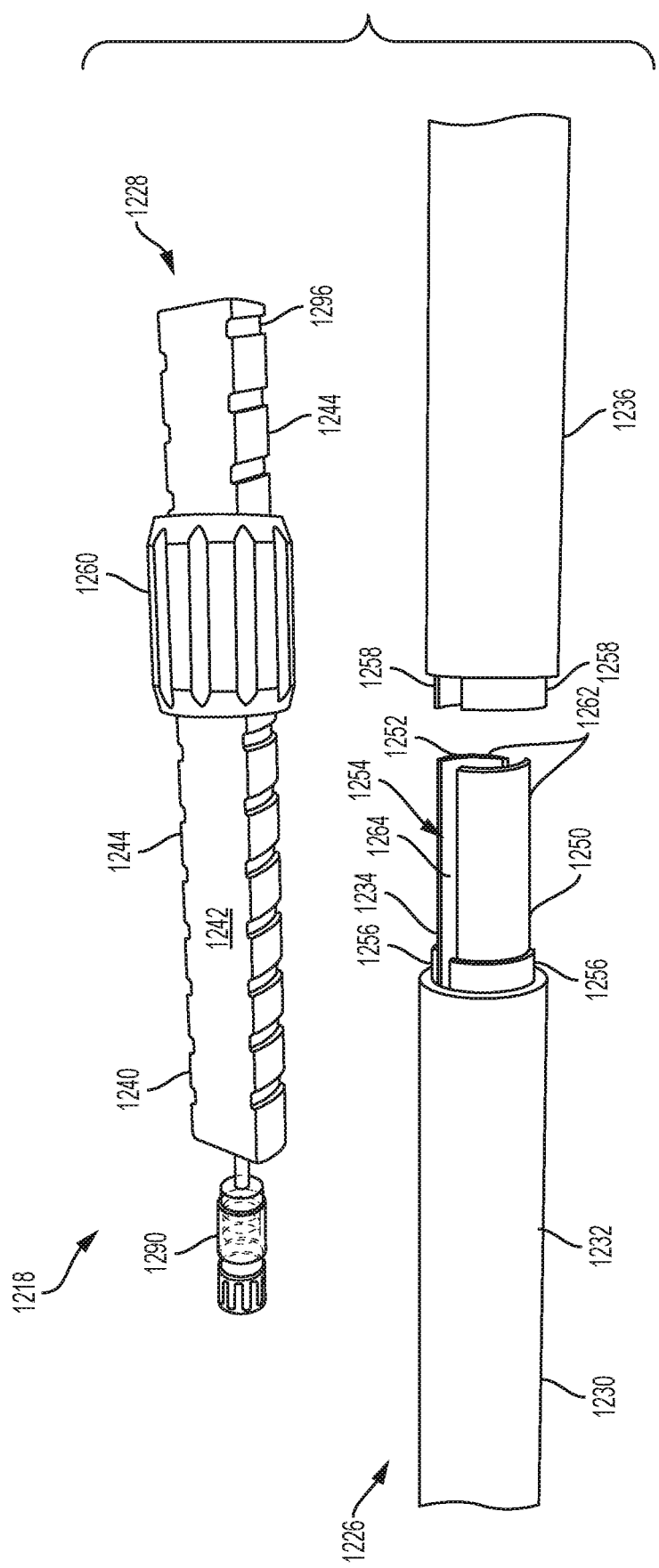
FIG. 13I is a detail exploded view of the handle of FIG. 12A.

Referring briefly to FIGS. 13H-13J, to facilitate assembly of the base 1226, each clearance surface 1262 may be monolithically coupled with the first bearing surface 1256, 1258. After positioning the shaft 1240 within the frame 1230 and the control element 1260 over the first bearing surface 1256, 1258 and the clearance surface 1262, each clearance surface 1262 may couple to the second bearing surface 1256, 1258 via, for example, press fit, one or more adhesives, snap connectors (not shown), or the like.

Referring to FIGS. 14A, 14F, and 14G, the distal portion 1236 of the frame 1230 may be similar to the proximal portion 1232 of the frame 1230. That is, the distal portion 1236 defines a distal passageway 1266 aligned with the opening 1254 for translatably receiving the shaft 1240. Referring specifically to FIGS. 14F, 14G, and 15 and in a similar manner to the proximal passageway 1238, the distal passageway 1266 may include a first key feature that, by coupling to the second key feature of the shaft 1240, inhibits rotation of the shaft 1240 relative to the frame 1230. For example, the second key feature of the shaft 1240 may be a non-circular cross-sectional area, and the first key feature of the distal passageway 1266 may be a cross-sectional area that is approximately identical to the cross-sectional area of the shaft 1240, or a cross-sectional area that is approximately identical to a portion of the cross-sectional area of the shaft 1240. In accordance with the specific example described above and as shown in FIGS. 14F, 14G, and 15, the distal passageway 1266 includes a cross-sectional area that is approximately identical to a portion of the cross-sectional area of the shaft 1240. Specifically, the distal passageway 1266 is defined by four opposing flat side surfaces 1268 and two opposing arcuate side surfaces 1270. The flat side surfaces 1268 and the arcuate side surfaces 1270 engage the flat side surfaces 1242 and the arcuate side surfaces 1244 of the shaft 1240, respectively, to permit relative longitudinal translation, but inhibit relative rotation and transverse translation of the shaft 1240 relative to the frame 1230. In the present example, the distal passageway 1266 is also defined by two additional opposing arcuate side surfaces 1272 that extend between the flat side surfaces 1268. The arcuate side surfaces 1272 are disposed apart from the shaft 1240 to reduce sliding friction between the shaft 1240 and the frame 1230.

Referring again to FIGS. 12A-14G, at its proximal end, the frame 1230 couples to a proximal cover 1276 (for example, via press fit, one or more adhesives, or the like). The proximal cover 1276 includes a proximal aperture 1278 (see FIGS. 13F and 13G) for permitting the electrode catheter 1212 to extend into the frame 1230. At its distal end, the frame 1230 couples to a distal cover 1280 (for example, via press fit, one or more adhesives, or the like). The distal cover 1280 includes a distal aperture 1282 (see FIGS. 13F and 13G) for permitting the electrode catheter 1212 to extend out of the frame 1230 and into the sheath 1216. The distal aperture 1282 press-fittingly receives a tube 1284 (for example, a hypotube 1284) that extends into the shaft 1240 and receives the electrode catheter 1212. The distal aperture 1282 also press-fittingly receives a distal coupling 1286 that detachably and sealingly couples to the proximal coupling 1222 of the sheath 1216 of the balloon catheter.

Referring now to FIGS. 12A and 13A-13J, the drive mechanism 1228 generally includes the shaft 1240 and the control element 1260. Referring specifically to FIGS. 13F-13J, the shaft 1240 includes a shaft passageway 1288 for permitting the electrode catheter 1212 to extend through the shaft 1240 and for receiving the tube 1284. The shaft 1240 passageway 1288 press-fittingly receives a proximal coupling 1290 that detachably and sealingly couples to the proximal coupling 1220 of the electrode catheter 1212. As such, movement of the control element 1260 relative to the base 1226 causes the shaft 1240 to translate within the base 1226, the electrode catheter 1212 thereby translates within the lumen of the sheath 1616 and translates within the balloon.

The shaft 1240 passageway 1288 also receives a seal 1292, for example, an O-ring, which translatably engages the outer surface of the tube 1284. As such, the seal 1292 inhibits the liquid in the shaft 1240 passageway 1288 (received from the sheath 1216 via the distal coupling 1286 and the hypotube 1284) from exiting the shaft 1240 by flowing between the shaft 1240 and the tube 1284.

As described briefly above, the control element 1260 is rotatably supported by the frame 1230. The control element 1260 includes a first engagement feature that couples to a second engagement feature of the shaft 1240 such that rotation of the control element 1260 relative to the base 1226 causes translation of the shaft 1240 relative the base 1226 (and translation of the electrode catheter 1212 within the lumen of the sheath 1216 and within the balloon). For example and as shown in the Figures, the first engagement feature may be a first threaded surface 1294 within the control element 1260, and the second engagement feature may be a second threaded surface 1296 formed on the arcuate side surfaces 1244 of the shaft 1240. Stated differently, the shaft 1240 may include a second, interrupted threaded surface that extends from the opening 1254 in the frame 1230 to engage the first threaded surface 1294 of the control element 1260. In any case, rotation of the control element 1260 and the first threaded surface 1294, together with the shaft 1240 being rotatably fixed within the frame 1230, causes translation of the second threaded surface 1296 and the shaft 1240 relative to the frame 1230 (and translation of the electrode catheter 1212 within the lumen of the sheath 1216 and within the balloon).

For certain applications, it may be desirable to increase the amount and/or the size of cavitation bubbles produced along with a pressure wave that is generated by introducing electrical energy, via an electrode assembly, into a corresponding liquid medium. For example, when entering smaller diameter sized blood vessels, the size of the catheter may be limited. In some cases, the force that cavitation bubbles exert on tissue (for example, a vascular occlusion) may be proportional to the size of the individual cavitation bubbles created, as the bubbles expand and contract after one or more electrical pulses are introduced into the liquid medium and a pressure wave is generated. That is, the strength of the initial pressure wave and/or the size of the cavitation bubble may be limited with the use of a non-gas saturated liquid medium. One manner by which the size of individual cavitation bubbles can be increased (for example, to impart greater amount of force on a particular tissue) is to saturate the liquid medium with gaseous substances so that the gas within the liquid medium exhibits a higher vapor pressure as compared to that of the liquid medium without such gas. Suitable gaseous substances that may be used to create gas-saturated liquid medium include, but are not limited to, ambient air, carbon dioxide, iodine gas, oxygen, nitrogen, compressed air, nitrous oxide, and combinations of these.

The higher vapor pressure of the gaseous substance added to the liquid medium will cause the gaseous substance to return to a gaseous state faster (under smaller pressure fluctuations) than the liquid medium. In other words, less pressure is required to cause the saturated gaseous substances to come out of solution, resulting in the creation of larger cavitation bubbles, and concomitantly, a greater amount of force. In some cases, the use of gas-saturated liquid medium allows for the use of electrical energy at decreased intensities, or decreased pulses or pulse durations, without any accompanying decrease in the overall force generated by the cavitation bubbles (as each cavitation bubble is larger). This can enhance both the safety and efficacy of the procedure being performed.

The gaseous substances can be imparted to the liquid medium through various means, including under pressure, through mechanical agitation, and/or by bubbling the gas into the liquid medium. In some cases, gas-saturated liquid medium can be prepared prior to a procedure and then injected into a catheter balloon prior to performing the procedure. Additionally or alternatively, gaseous substances can be delivered into that liquid medium that is already present in the catheter balloon.

The gases and/or gaseous substances may be dissolved and quantified by the amount of gases present in a 1 kg of the liquid medium. The maximum amount of gas that will dissolve in the liquid medium is dependent on the solubility of the particular gas in that liquid medium, the pressure, and the temperature as described by Henry's law of gas solubility. For example, carbon dioxide may be dissolved into water at a concentration of 1.25 g/kg of water or less at 30 degrees Celsius under atmospheric pressure. And upon dissolving carbon dioxide into water or saline, an overall concentration between 0.25-3.5 g/kgH2O is produced. The concentrations of other dissolved gases in a kilogram of liquid medium ranges from 1 mg-1 g/kg for iodine, 5-80 mg/kg for oxygen, 5-40 mg/kg for nitrogen, 5-500 mg/kg for room air, and 0.1-4 g/kg for nitrous oxide.

The gases and/or gaseous substances may be dissolved in quantities above the theoretical limit, which is known as super saturation. The theoretical limit is described by Henry's law as mentioned previously. By dissolving the gases under increased pressure or decreased temperature and then returning it to normal atmospheric conditions, it is possible to dissolve a larger quantity of gas then is possible at atmospheric conditions. For example, 2.5 g of carbon dioxide may be dissolved into 30 degrees Celsius water under 2 atm of pressure, and then returned to atmospheric pressure. For any dissolved gas, the saturation percentage is defined by the concentration of gas over the theoretical maximum concentration. For any of the previously mentioned gases in a supersaturated solution, the saturation percentage can range from 100-300 percent.

The use of a gas saturated liquid medium or super saturated liquid medium may also increase the initial pressure wave caused by the interaction of the electrical pulse and the liquid medium. That is, the gas saturated liquid medium or super saturated liquid medium may contain larger potential energy, which when activated by the electrical pulse, may create a larger initial pressure wave in comparison to a pressure wave created by the interaction of an electrical pulse and a non-gas saturated liquid medium.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter to disrupt a vascular obstruction in a patient, the catheter comprising:
   a sheath having a guidewire lumen, an inflation lumen, a proximal end and a distal end;
   a balloon assembly circumferentially arranged around a portion of the sheath, the balloon assembly being expandable and contractable;
   one or more liquid medium ports disposed within the sheath and within the balloon assembly to thereby deliver a liquid medium to the balloon;
   at least one electrode assembly comprising at least two electrodes disposed within the balloon assembly adjacent to the guidewire lumen, wherein the at least one electrode assembly is coupled to an electrical generator that delivers pulses of voltage across the at least two electrodes to thereby create electrical arcs between the at least two electrodes within the liquid medium, wherein the electrical arcs produce pressure waves and cavitation bubbles in the liquid medium that expand the balloon assembly and thereby disrupt the portion of the vascular obstruction; and a pressure-wave reflective element affixed to an exterior of the balloon assembly such that the pressure-wave reflective element is expandable and contractable with the balloon assembly, wherein the pressure-wave reflective element comprises a scaffolding structure and a plurality of openings, wherein the scaffolding structure is configured to constrain expansion of the balloon assembly and thereby attenuate the pressure wave passing to the vascular obstruction, and wherein the openings in the scaffolding structure are configured to reduce passage of the cavitation bubbles in the liquid medium through the openings to an exterior of the pressure-wave reflective element.

2. The catheter of claim 1, wherein the balloon assembly has an exterior, and wherein the pressure-wave reflective element is disposed on the exterior of the balloon assembly.

3. The catheter of claim 1 wherein the openings of the scaffolding are sized to be smaller than the cavitation bubbles produced in the liquid medium by the at least two electrodes.

4. The catheter of claim 1, wherein the plurality of openings comprise at least one of the following shapes: circle; oval; triangle; square; rectangle; polygon; diamond; pentagon; hexagon; heptagon; octagon; nonagon; and decagon.

5. The catheter of claim 1, wherein the liquid medium is contrast medium or contrast solution.

6. The catheter of claim 5, wherein the liquid medium is contrast medium including any one of iodine-containing contrast medium or gadolinium contrast medium.

7. A catheter to disrupt an obstruction in a vasculature of a patient, the catheter comprising:

a sheath having a guidewire lumen, an inflation lumen, a proximal end and a distal end;

a balloon assembly circumferentially arranged around a portion of the sheath, the balloon assembly having an exterior that is expandable and contractable within the vasculature of the patient;

one or more liquid medium ports disposed within the sheath and within the balloon assembly to thereby deliver a liquid medium to the balloon;

at least two electrodes disposed within the balloon assembly adjacent to the guidewire lumen, wherein the at least two electrodes are coupled to an electrical generator that delivers pulses of voltage across the at least two electrodes to thereby create electrical arcs between the at least two electrodes within the liquid medium, wherein the electrical arcs produce pressure waves and cavitation bubbles in the liquid medium that expand the balloon assembly and thereby disrupt at least a portion of the obstruction in the vasculature of the patient; and a pressure-wave reflective element affixed to an exterior of the balloon assembly such that the pressure-wave reflective element is expandable and contractable with the balloon assembly, wherein the pressure-wave reflective element comprises a scaffolding structure and a plurality of openings, wherein the scaffolding structure is configured to constrain expansion of the balloon assembly and thereby attenuate the pressure wave passing to the vascular obstruction.

8. The catheter of claim 7 wherein the openings in the scaffolding structure are configured to reduce passage of the cavitation bubbles in the liquid medium through the openings to an exterior of the pressure-wave reflective element.

* * * * *